US008785720B2

(12) United States Patent
Hoogstraten et al.

(10) Patent No.: US 8,785,720 B2
(45) Date of Patent: *Jul. 22, 2014

(54) METHODS FOR COUPLING RESISTANCE ALLELES IN TOMATO

(75) Inventors: Jacobus Gerardus Joannes Hoogstraten, Wageningen (NL); Carl J. Braun, III, Woodland, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 677 days.

This patent is subject to a terminal disclaimer.

(21) Appl. No.: 12/503,595

(22) Filed: Jul. 15, 2009

(65) Prior Publication Data

US 2010/0212048 A1 Aug. 19, 2010

Related U.S. Application Data

(63) Continuation of application No. 11/056,548, filed on Feb. 11, 2005, now Pat. No. 7,615,689, and a continuation-in-part of application No. 10/777,984, filed on Feb. 12, 2004, now abandoned.

(51) Int. Cl.
*A01H 1/04* (2006.01)
*A01H 5/00* (2006.01)
*A01H 5/08* (2006.01)
*A01H 5/10* (2006.01)
*C12Q 1/68* (2006.01)

(52) U.S. Cl.
CPC .............. *A01H 1/04* (2013.01); *C12Q 1/6895* (2013.01); *A01H 5/08* (2013.01)
USPC .......... 800/265; 800/267; 800/269; 800/317.4

(58) Field of Classification Search
None
See application file for complete search history.

(56) References Cited

U.S. PATENT DOCUMENTS

| | | | |
|---|---|---|---|
| 5,850,009 A | 12/1998 | Kevern | |
| 6,414,226 B1 | 7/2002 | Hoogstraten | |
| 7,615,689 B2 | 11/2009 | Hoogstraten et al. | |
| 2005/0278804 A1 | 12/2005 | Hoogstraten et al. | |

FOREIGN PATENT DOCUMENTS

WO WO 2005/079342 A2 9/2005

OTHER PUBLICATIONS

Veremis et al. Theoretical and Applied Genetics 98: 274-280 (1999).*
Ammiraju et al., "The heat-stable root-knot nematode resistance gene Mi-9 from Lycopersicon peruvianum is localized on the short arm of chromosome 6," Theor Appl Genet 106:478-484 (2003).
AVRDC Report 2002, AVRDC—The World Vegetable Center, pp. 9-11 (2003).
Barone, "Molecular Marker-Assisted Selection for Resistance to Pathogens in Tomato," Marker Assisted Selected: A Fast Track to Increase Genetic Gain in Plant and Animal Breeding? Session I:MAS in Plants, pp. 29-35 (posted Oct. 17-18, 2003).
Chagué et al., "Identification of RAPD markers linked to a locus involved in quantitative resistance to TYLCV in tomato by bulked segregant analysis," Theor Appl Genet 95:671-677 (1997).
Czosnek et al., "A worldwide survey of tomato yellow leaf curl viruses," Arch Virol 142:1391-1406 (1997).
European Search Report issued in EP 05075318.5 dated May 23, 2005.
Freitas-Astua et al., "Traditional and Transgenic Strategies for Controlling Tomato-Infecting Begomoviruses," Fitopatol. Bras., 27(5):437-449 (2002).
Gómez et al., "Breeding for resistance to begomovirus in tropic-adapted tomato genotypes," Plant Breeding 123:275-279 (2004).
Ho et al., "The Root-Knot Nematode Resistance Gene (Mi) in Tomato: Construction of a Molecular Linkage Map and Identification of Dominant cDNA Markers in Resistant Genotypes," The Plant Journal: For Cell and Molecular Biology, 2(6):971-982 (1992).
International Search Report issued in PCT/US05/04547 dated Jun. 22, 2006.
Kaloshian et al., "Genetic and Physical Localization of the Root-Knot Nematode Resistance Locus Mi in Tomato," Molecular and General Genetics, 257(3):376-385 (1998).
Mansoor et al., "Geminivirus Disease Complexes: An Emerging Threat," TRENDS in Plant Science, 8(3):128-134 (2003).
Marker TG36 (SGN-M24), http://www.sgn.cornell.edu/search/markers/markerinfo.pl?marker_id=24 (Jan. 17, 2007) (1 page).
Maruthi et al., "Comparison of resistance to *Tomato leaf curl virus* (India) and *Tomato yellow leaf curl virus* (Israel) among *Lycopersicon* wild species, breeding lines and hybrids," European Journal of Plant Pathology 109:1-11 (2003).
Meija et al., "Summary of Field Evaluations of Tomato Germplasm in Sanarate Guatemala, Mar. 2003," retrieved from the internet: URL: http://www.plantpath.wisc.edu/GeminivirusResistantTomatoes/CDR/Mar03/Field03/htm (posted in Apr. 2003).
Milligan et al., "The Root Knot Nematode Resistance Gene Mi from Tomato is a Member of the Leucine Zipper, Nucleotide Binding, Leucine-Rich Repeat Family of Plant Genes," The Plant Cell, 10:1307-1319 (1988).
Morales, "Conventional Breeding for Resistance to Whitefly-Transmitted Geminiviruses," Virologist, International Center for Tripical Agriculture (CIAT), AA 6713, Cali, Columbia, 25 pages, (2001).
Moretti et al., "Introgression of Resistance Against Mi-1-virulent *Meloidogyne* spp. From *Lycopersicon peruvianum* into *L. esculentum*," Research Reports, TGC Report 52, pp. 21-22 (2002).
Navot et al., "Tomato Yellow Leaf Curl Virus: A Whitefly-Transmitted Geminivirus with a Single Genomic Component," Virology 85:151-161 (1991).
Pan et al., "Comparative Genetics of Nucleotide Binding Site-Leucine Rich Repeat Resistance Gene Homologues in the Genomes of Two Dicotyledons: Tomato and Arabidopsis," Genetics, 155:309-322 (2000).
Poehlman et al., Breeding Field Crops, 4th ed., Iowa State University Press (Ames, Iowa), p. 473 (1995).

(Continued)

Primary Examiner — David T Fox
(74) Attorney, Agent, or Firm — Matthew L. Madsen; Arnold & Porter LLP

(57) ABSTRACT

A *Lycopersicon esculentum* plant comprising within its genome at least one tomato yellow leaf curl virus (TYLCV) resistance allele and at least one root knot nematode resistance allele, characterized in that the resistance alleles are present in coupling phase at different loci on one chromosome and in that the plant is highly resistant both against TYLCV and to at least one root knot nematode species selected from the group consisting of *Meloidogyne arenaria, Meloidogyne incognita* and *Meloidogyne javanica*.

28 Claims, 3 Drawing Sheets

(56) References Cited

OTHER PUBLICATIONS

Rossi et al., "The Nematode Resistance Gene Mi of Tomato Confers Resistance Against the Potato Aphid," Proc. Nat'l Acad. Sci., 95:9750-9754 (1998).
Rubio et al., "A new approach to evaluate relative resistance and tolerance of tomato cultivars to begomoviruses causing the tomato yellow leaf curl disease in Spain," Plant Pathology 52:763-769 (2003).
Santana et al., "Sources of resistance in Lycopersicon spp. To a bipartite whitefly-transmitted geminivirus from Brazil," Euphytica 122:45-51 (2001).
Scott et al., "A New Allele at the Potato Leaf Locus Derived from L. Chilense Accession LA 1932 is Discovered in a Geminivirus Resistance Project," Research Reports, TGC Report 52, pp. 31-36 (2002).
Tanksley et al., "High Density Molecular Linkage Maps of the Tomato and Potato Genomes," Genetics, 132:1141-1160 (1992).
Tripathi et al., "Identification of sources of resistance in Lycopersicon species to Tomato leaf curl geminivirus (ToLCV) by agroinoculation," Euphytica 129:43-52 (2002).
van Daelen et al., "Long-range physical maps of two loci (Aps-1 and GP79) flanking the root-knot nematode resistance gene (Mi) near the centromere of tomato chromosome 6," Plant Molecular Biology 23:185-192 (1983).
Varma et al., "GE Tomato Resistant to Leaf Curl Disease," http://www.isb.vt.edu/articles/jun0603.htm (Jan. 24, 2007) (2 pages).
Vidaysky et al., "Tomato Breeding Lines Resistant and Tolerant in Tomato Yellow Leaf Curl Virus Issued from Lycopersicon hirsutum," Phytopathology, 88(9):910-914 (1998).
Weide et al., "Integration of the Classical and Molecular Linkage Maps of Tomato Chromosome 6," Genetics, 135:1175-1186 (1993).
Williamson et al., "A PCR-Based Marker Tightly Linked to the Nematode Resistance Gene, Mi, in Tomato," Theoretical and Applied Genetics, 87(7):757-763 (1994).
Zamir et al., "Mapping and Introgression of a Tomato Yellow Leaf Curl Virus Tolerance Gene, TY-1," Theoretical and Applied Genetics, 88(2):141-146 (1994).
Doganlar et al., "Production of interspecific $F_1$ hybrids, $BC_1$, $BC_2$ and $BC_3$ populations between Lycopersicon esculentum and two accessions of Lycopersicon peruvianum carrying new root-knot nematode resistance genes," Euphytica, 95:203-207 (1997).
Seah et al., "The nematode-resistance gene, Mi-1, is associated with an inverted chromosomal segment in susceptible compared to resistant tomato," Theoretical and Applied Genetics, 108:1635-1642 (2004).
Yaghoobi et al., "Mapping a new nematode resistance locus in Lycopersicon peruvianum," Theoretical and Applied Genetics, 91:457-464 (1995).
Zhong et al., "FISH to meiotic pachytene chromosomes of tomato locates the root-knot nematode resistance gene Mi-1 and the acid phosphatase gene Aps-1 near the junction of euchromatin and pericentromeric heterochromatin of chromosome arms 6S and 6L, respectively," Theoretical and Applied Genetics, 98:365-370 (1999).
Behare et al., "Restriction Fragement Length Polymorphism Mapping of the Stemphylium Resistance Gene in Tomato," Molecular Plant-Microbe Interactions, 4(5):489-492 (1991).
Huang et al., "Development of diagnostic PCR markers closely linked to the tomato powdery mildew resistance gene Ol-1 on chromosome 6 of tomato," Theor Appl Genet, 101:918-924 (2000).
Jones et al., "Two Complex Resistance Loci Revealed in Tomato by Clasical and RFLP Mapping of the Cf-2, Cf-4, Cf-5, and Cf-9 Genes for Resistance to Cladosporium fulvum," Molecular Plant-Microbe Interactions, 6(3):348-357 (1993).
Kenyon et al., Pathogenicity mutants of the tomato leaf mould fungus Fulvia fulva (Cooke) Ciferri (syn. Cladosporium fulvum Cooke), Physiological and Molecular Plant Pathology, 43:173-191 (1993).
Maeda, "Studies on Breeding of Varieties Resistant to Root-Knot Nematodes (Meloidogyne incognita var. acrita) in Tomatoes," Bulletin of the Tokyo Metropolitan Agricultural Experiment Station, Report No. 3, 14 pages (1964) (with English translation).
Nakajima, "New plant-breeding technology," Yokendo, $2^{nd}$ Ed., p. 281 (1991) (with English translation).
Ori et al., "A genomic search for the gene conferring resistance to fusarium wilt in tomato," Euphytica, 79:201-204 (1994).
Peleman et al., "The challenges in Marker Assisted Breeding," Eucarpia Leafy Vegetables, 2003:125-130 (2003).
Third Party Submission filed on Feb. 17, 2012, in Japanese Patent Application No. 2005-033928 (with English translation).
Third Party Submission filed on Feb. 17, 2012, in Japanese Patent Application No. 2010-226321 (with English translation).
Yamakawa, "Vegetables / Resistant Cultivars and their Uses," Zenkoku Nōson Kyōiku Kyōkai, 9 pages (1978) (with English translation).
Extended European Search Report issued in EP 10012145.8 on Jun. 21, 2011.
Osborn et al., "Insights and Innovations from Wide Crosses: Examples from Canola and Tomato," Crop Sci., 47(Suppl.3):S228-S237 (2007).

* cited by examiner

Figure 1

```
     taatccgtcgttacctctcctt (SEQ ID NO: 1)
  1  CTAATCCGTCGTCGTTACCTCTCCTTGAACTAAAATTTTTGTCAAAAGTT          Ty-1
  1  CTAATCCGTCGTCGTTACCTCTCCTTGAACTAAAATTTGTTGTCAAAAGTT         Ty+

51  ACAAATCTGTTATTTTATATATTTTTTCTTGGAATTACTATCGATAT             Ty-1
 51  ACAAATCTGTTATTTTATATACTTTTTCTTGGAATTACTATCTTTAT             Ty+

101  TTTTGTAATTAGAAGGTTAGAATTGGAGTATATATGTTGTGATTGGAACG          Ty-1
100  TTTTGTAATTAGAAGGTTAGAATTGGAGTATATATGTTGTGATTGGACCG          Ty+

151  ATTTGTGTTGCCTTTATGGTGGCAATTATGTTTACATGTGTCATTGGCT           Ty-1
150  AGTTGCTATTGCCTTTATGGTGGAAATTATGTTTACATGTGTCATTGGGT          Ty+

201  AACTTACTGAGTCATCTTACTTTTTAATAAGAATGCTTCAAATGTTTAT           Ty-1
200  AACTTACTGAGTCATCTTACTTTTTTAATAAGAATGCTTCAATGTTTAT           Ty+

251  AATTTCATTAGCTCAATGGTAATTGTATTTATTGATGCATATATCTTTT           Ty-1
250  AATTCCATTAGCTCAATGGTATTGTATTTATTGATGCATATATCTTTT            Ty+

301  TGTTCTAGTTTCTGATTATATCATGTANCGAAACTTATATATAAAAATAAT         Ty-1
300  TGTTCTAGTTTCTGATTATATCATGTAGCGAAACTTATATATAAAAATAAA         Ty+

351  TAGTAATAGTAGTAGAANATTATGACATCATTGCTATTGAAGTCATCCG           Ty-1
350  TAGTAATAGTAGTAGATAATTATGACATCATTGCTATTGAAGTCATCCG           Ty+
             (SEQ ID NO: 2)  agtaacgataacttcagtagc 401  GAATCT                                                      Ty-1
399  GAATCTANC                                                   Ty+
```

Figure 2

```
  1  GACACGGACCCACTATTCTGAAACTGATGTCATTCTTTCTCTCCTTATCGGAGCCTTGGTCTGAGTTTCCAGTCTTGCAAGCAAATGACTAGCTTGAC  Mi+
  1  GACACGGACCCACTATTCTGAAACCGATGTCATTCTTTCTCTCCTTATCGGAGCCTTGGTCTGAATTTCCGTCTTGCAAGCAAATGACTAGCTTGAC  Mi-1
  1  GACACGGACCCACTATTCTGAAACTGATGTCATTCTTTCTCTCCTTATCGGAGCCTTGGTCTGACTTTCCAGTCTTGCAAGCAAATGACTAGCTTGAC  Mi-J

101  GTAAGGATCTGCACTTACATCGGTATCCTGTTGAGTTGCATAACCAGAAACCTGGACTTTGCTTTGACTTTTTTACCTGATTCACGATGACATCTTT  Mi+
101  GTAAGGGATCTGCACTTGCATCGGTATCCTGTTGAGTTGCATAACCAGAAACCTGGACTTTGCTTTGACTTTTTTACCTGATTCACGATGGACATCTTT  Mi-1
101  GTAAGGGATCTGCACTTACATCGGTATCCTGTTGAGTTGCATAACCAGAAACCTGGACTTTGCTTTGACTTTTTTACCTGATTCACGATGGACAACTTT  Mi-J

201  CTCCTCTAATTCAGCTTCAGATAATAGATCATTAACTCTTGCCATTGCAGGCATTATCCTTCTTAACCATACTGGATTATTGGAGAACTCATCATTTCA  Mi+
201  CTCCTCTAATTCAGCTTCAGATAATAGATCATTAACTCTTGCCATTGCAGGCATTATCCTTCTTAACCATACTGGATTATTGGAGAACCCATCATTTCA  Mi-1
201  CTCCTCTAATTCAGCTTCAGATAATAGATCATTAACTCTTGCCATTGCAGGCATTATCCTTCTTAACCATACTGGATTATTGGAGAACCCATCATTTCA  Mi-J

301  CCATCAGAAGACTCTTGGGACTAGAAGTGGGTAAGGCTGAAGAGGAGCAACAGAAGTCGCGAATTGCATAGATCCTTTGTGAAGAATCTGCAGCTT  Mi+
301  CCATCAGAAGACTCTTGGGGACTAGAAGTGGGGAAGGCTGAAGAGGAGCAACAGAAGTCGCGAATTGCATAGATCCTTTGTGAAGAATCTGCAGCTT  Mi-1
301  CCATCAGAAGACTCTTGGGACTAGAAGTGGGTAAGGCTGAAGAGGAGCAACAGAAGTCGCGAATTGCATAGATCCTTTGTGAAGAATCTGCAGCTT  Mi-J

401  TAACACTCAACAAAGATAGAGTACTATCCAGATCTTGCCCAGCCTGCTGTTCCTTTTTAACTTGACCTGTTCCAGCACTACCTTTGCTTGCACTAGTGTC  Mi+
401  TAACACTCAACAAAGATAGAGTACTATCCAGATCTTGCCCAGCCTGCTGTTCCTTTTTAACTTGACCTGTTCCAGCACTACCTTTGCTTGCACTAGTGTC  Mi-1
401  TAACACTCAACAAAGATAGAGTACTATCCAGATCTTGCCCAGCCTGCTGTTCCTTTTTAACTTGACCTGTTCCAGCACTACCTTTGCTTGCACTAGTGTC  Mi-J

501  CTTCCGGTCAGACAAGGAGACCCTTGCTACCTTTTCCTTTTCCTTCCTAGAGATGTCATCACATATTTTTCCATAGAATCGTGGGATTACATGTCAAGGAATCT  Mi+
501  CTTCCGGTCAGACAAGGAGACCCTTGCTACCTTTTCCTTTTCCTGAGATGTCATCACATATTTTTCCATAGAATCTGGGGATTACATGTCAAGGAATCT  Mi-1
501  CTTCCGGTCAGACAAGGAGACCCTTGCTACCTTTTCCTTCCTGAGATGTCATCACATATTTTTCCATAGAATCGTGGGGATTACATGTCAAGGAATCT  Mi-J

601  GCATTCTCCCCTTTCTTCTTAATCGGAGAATCATTATTGTCACACTTCCCCCTTATGCGTTGACACATGGAAATAAGCTTCTGGGTTCTTGCTG  Mi+
601  CGAGTTCTCCCCTTTCTTCTTAATCGGAGAATCATTATTGTCACACTTCCCCCTTATGCGTTGACACATGGAAATAAGCTTCTGGGTTCTTGCTG  Mi-1
601  CGTAGTTCTCCCCTTTCTTCTTAATCGGAGAATCATTATTGTCACACTTCCCCCTTATGCGTTGACACATGGAAATAAGCTTCTGGGTTCTTGCTG  Mi-J

701  AAACCAAGTCTTTCTTCTTTGAATCATCCTCTGAGTCCCTGTTCTTACATTGTCAGATCATCTCGGCATTTACTGCTTGAACTCCATCTAGACTTTC  Mi+
701  AAACCAAGTCTTTCTTCTTTGAATCATCCTCTGAGTCCCTGTTCTTACATTGTCAGATCATCTCGGCATTTACTGCTTGAACTCCATCTAGACTTTC  Mi-1
701  AAACCAAGTCTTTCTTCTTTGAATCATCCTCTGAGTCCCTGTTCTTACATTGTCAGATCATCTCGGCATTTACTGCTTGAACTCCATCTAGACTTTC  Mi-J

801  AACAACAGGGCATTAAGGTCTGGTTCTCGTTCGTCATCAGTGCATCATCCTGTATAATTTTTTGGAAGATACATCATCTGATTCCACTTCACTTGTGTTCCTTCTA  Mi+
801  AACAACAGGGCAGAAGGTCTGGTTCTCGTTCGTCATCAGTGCATCATCCTGTATAATTTTTTGGAAGATACATCATCTGATTCCACCTCACTTGTGTTCCTTCTA  Mi-1
801  AACAACAGGGCAGAAGGTCTGGTTCTCGTTCGTCATCAGTGCATCATCCTGTATAATTTTTTGGAAGATACATCATCTGATTCCACCTCACTTGTGTTCCTTCTA  Mi-J

901  TTTGCATCCTCCGTAG  Mi+
901  TTTGCATCCTCCGTAG  Mi-1
901  TTTGCATCCTCCGTAG  Mi-J
```

METHODS FOR COUPLING RESISTANCE ALLELES IN TOMATO

CROSS REFERENCE TO RELATED APPLICATION

This application is a continuation of application Ser. No. 11/056,548 filed Feb. 11, 2005, now U.S. Pat. No. 7,615,689, which is hereby incorporated by reference in its entirety, application Ser. No. 11/056,548 filed Feb. 11, 2005, is a continuation-in-part of application Ser. No. 10/777,984 filed Feb. 12, 2004 (abandoned).

INCORPORATION OF SEQUENCE LISTING

A paper copy of the Sequence Listing and a computer-readable form of the sequence listing submitted in parent application Ser. No. 11/056,548 filed Feb. 11, 2005, containing a file which is 7,638 bytes in size (measured in MS DOS), and which was created on Aug. 10, 2005, are herein incorporated by reference.

TECHNICAL FIELD OF THE INVENTION

The present invention relates to methods for pyramiding tightly-linked genes of commercial importance in tomato (*Lycopersicon esculentum*, L.). Specifically, the invention relates to creating tomato plants comprising the most effective Tomato yellow leaf curl virus resistance gene (Ty-1) and the most effective nematode resistance gene (Mi-1) in coupling phase (in cis), such that these closely linked genes are co-inherited as if a single unit.

BACKGROUND OF THE PRESENT INVENTION

There are over two hundred documented diseases of cultivated tomato (Compendium of Tomato Diseases. J. B. Jones, J. P. Jones, R. E. Stall, T. A. Zitter, editors, (1997) American Phyto-pathological Society Press, St. Paul, Minn.). To combat the damage caused by these pathogens, growers typically employ an integrated pest management strategy including both cultural practices and pesticide use. An example of a cultural practice is the use of netting over tomato plants, which provides a physical barrier that can be effective in excluding disease-bearing insects from infecting the crop.

Despite numerous research studies that have demonstrated efficacious transgenic approaches against plant diseases, there are currently no transgenic tomato varieties available to the grower that are resistant to any pathogens. Further, there remains an issue of public resistance, particularly in the European Union, which, combined with the high cost of obtaining regulatory approval, have effectively prohibited this promising technology from being used in commercial tomato cultivation.

Introgression of disease resistance genes into modern cultivars using traditional breeding approaches has remained an effective technology available for combating the majority of plant diseases. Because of its continued success, the approach is still a primary focus in both academic and commercial tomato breeding programs.

Among the hundreds of tomato pathogens, diseases caused by nematodes and the Tomato yellow leaf curl virus (TYLCV) are among the most important to the commercial grower. Nematodes are pandemic and their distribution extends nearly from pole to pole. In addition to their widespread distribution, various species of nematodes are etiological agents with diverse host ranges, including most plants and animals. For example, nematodes cause diseases as diverse as a pinworm disease in humans (*Enterobius vermicularis* is the etiological agent) to a root-knot disease in tomatoes. Although there are more than fifty species of root knot nematodes, the three most important species infecting tomato are *Meloidogyne arenaria*, *M. incognita* and *M. javanica*.

Root knot species of nematodes are named for the type of root structure their infection produces in the plant. Upon successful infection, the nematode produces elicitors that result in the plant thickening its roots, resulting in the production of 1 mm to 10 mm lumps or galls on the roots. These changes facilitate the transport of nutrients from the plant to the nematode. The infected and morphologically altered roots have a concomitantly diminished capacity to supply water and nutrients to the plant. Plants manifest this reduced capacity for nutrient uptake with a general reduction of vigor that can be observed above ground. Infected plants may also display more specific symptoms such as stunting, wilting and chlorosis. As the nematode population builds up during the growing season, wilting becomes more pronounced and fruit set can be affected.

Chemical control of root knot nematodes is effective, and the nematicide methyl bromide provides excellent control for all of the *Meloidogyne* species. For various reasons, including health concerns for pesticide applicators and concern over ozone-depletion, the use of methyl bromide is being reduced around the world. An eventual ban of this chemical control agent highlights the importance of developing alternative methods to control nematode disease in tomatoes.

TYLCV is a geminivirus, and is classified in the Begomovirus group. Unlike the nematodes, which are ubiquitous in nearly all soil, the distribution of tomato yellow leaf curl virus is limited by the range of the insect vector that transmits the virus, the whitefly *Bemisia tabaci*.

Commercial tomato production has shifted over the past twenty five years from temperate to more tropical growing regions in the world, due to lower labor costs, better transportation and treaties like the North American Free Trade Agreement and the World Trade Organization Agreement. This shift in geography coincides with the distribution of *B. tabaci*. Thus, as tomato growing regions have shifted towards tropical climates, the disease caused by TYLCV has become more pronounced. TYLCV can be rapidly transmitted to tomatoes by the feeding of the whitefly. Once in the plant, the virus replicates and spreads throughout the plant, although it is typically limited to the phloem. TYLCV causes severe symptoms in the plant, ranging from leaf curling and yellowing, to a stunting caused by a shortening of the internode length and arrest in floral growth. Together, this results in plants with a bush-like appearance. Crop losses can be severe; during the early 1990's, approximately 95% of the tomato crop in the Dominican Republic was lost, and in a single season (1991-1992), an approximate 140 million dollar loss was reported in Florida (Moffat, Science (1999) 286:1835).

Chemical control of the whitefly can be effective, but the misuse of pesticides in commercial tomato production has resulted in pesticide-resistant *B. tabaci* that can vector over 20 different tomato-infecting begomoviruses (Morales, (2001), Crop Protection; Poiston and Anderson (1997) Plant Disease 81:1358-1369; Zeidan et al. (1999) Asia Trop. Res. Ext. 1:107-115).

Just as the leading chemical option for nematode control in tomatoes is being phased out, chemical control options for TYLCV are also being reduced, for reasons ranging from the insect vector becoming resistant to the pesticide to public health concerns over the use of pesticides. The high development costs attendant to producing transgenic resistant cultivars is likewise an impediment to the development of TYLCV resistant cultivars using a genetic engineering approach. Those skilled in the art will thus recognize the need for alternatives to these chemical control strategies and transgenic strategies for the control of nematode, geminivirus (TYLCV) and other plant diseases in tomato production. The introgression of naturally occurring resistance genes remains the most effective option for controlling tomato pathogens today.

Although the inheritance of a resistance phenotype can be quantitative and polygenic, it is common in plants to have many dominant to semi-dominant resistance genes controlled by individual single loci. Plant resistance genes often encode for proteins that act as receptors that bind specific pathogen-encoded ligands. This pathogen-specific recognition and subsequent response by the plant is a phenomena first described by Flor in the late 1940's and referred to as 'gene-for-gene' resistance, (reviewed by Flor (1971) Ann. Review of Phytopathology 9:275-296). This specific receptor-ligand complex triggers a signal transduction pathway that ultimately results in a resistance phenotype (Baker et al. (1997), Science 276: 726-733; Staskawicz et al. (1995) Science 268:661-667). In response to this recognition of pathogen attack, the host can respond with a strengthening of the cell wall, an oxidative burst, induction of defense gene expression and at times, rapid cell death at the infection site called the hypersensitive response.

For most breeding objectives, commercial breeders work with germplasm often referred to as the 'cultivated type'. This germplasm is easier to breed with because it generally performs well when evaluated for horticultural performance. The performance advantage the cultivated types provide is often offset by a lack of allelic diversity. This is the trade off a breeder accepts when working with cultivated germplasm—better overall performance, but a lack of allelic diversity. Breeders generally accept this trade off because progress is faster when working with cultivated material than when breeding with genetically diverse sources.

In contrast, when a breeder makes either wide intra-specific crosses or interspecific crosses, a converse trade-off occurs. In these examples, a breeder typically crosses cultivated germplasm with a non-cultivated type. In such crosses, the breeder can gain access to novel alleles from the non-cultivated type, but has to overcome the genetic drag associated with the donor parent. Besides this difficulty with this breeding strategy, this approach often fails because of fertility or fecundity problems.

There are many wild relatives that can be crossed with cultivated tomato, including *L. pennellii, L. hirsutum, L. peruvianum, L. chilense, L. parviflorum, L. chmielewskii, L. cheesmanii, L. cerasiforme,* and *L. pimpinellifolium*. The genetic distance between the wild species and the cultivated *L. esculentum* correlates with the difficulty of both making the interspecific cross, and successfully creating a new commercial cultivar with an added trait (Genetics and breeding. MA Stevens and CM Rick. In: The tomato crop: A scientific basis for improvement. J G Atherton and J Rudich, editors. Chapman and Hall, (1994), London). For example, species like *L. pimpinellifolium, L. cerasiforme, L. cheesmanii, L. chmielewskii* and *L. parviflorum* are the easiest wild species to use as donors for trait introgression into the modern tomato. In contrast, *L. pennellii, L. chilense, L. hirsutum* and *L. peruvianum* are far more difficult species for trait introgression into the modern tomato (ibidem). When using these more distantly related species, it is not uncommon to have to use bridging species and embryo rescue for early generation crosses. Even with these extra steps, one can face significant segregation distortion, fertility problems, reduced recombination and genetic drag. Even in advanced generations, a suppression of recombination in the introgressed area of the genome presents the primary obstacle to reducing the genetic drag enough to create a successful commercial cultivar.

Thus, even though one may identify a useful trait in a wild species and target that trait for introgression into the cultivated species, there is no guarantee of success. Most successful commercial tomato breeders work their entire careers without successfully completing an introgression from a wild species to create commercial cultivars. The barriers to success include segregation distortion, which may result in areas of the wild genome that can be difficult to impossible to introgress. Further, some of the wild species of the modern tomato are self-incompatable, meaning that they cannot self pollinate. As a result of the self-incompatability, these plants are highly heterogeneous, having different alleles at many loci. The highly heterogenous nature of these wild species can also hinder the introgression of the most efficacious allele of interest.

The difficulty with introgressing novel alleles from wild relatives of domesticated crops extends to many crops, and is exemplified in tomato by a nematode resistance introgression. Bailey ((1941) Proc. Am. Hort. Sci. 38:573-575) first identified the wild species *L. peruvianum* as a potential source for nematode resistance. Smith ((1944) Proc. Am. Soc. Hort. Sci. 44:413-416) later used embryo rescue to successfully recover an interspecific hybrid containing the nematode resistance trait. Gilbert and McGuire ((1955) coined this locus Mi, and subsequently mapped Mi to chromosome 6 (Gilbert (1958) Tomato Genet. Coop Rep. 8:15-17). The resistance allele at the Mi locus, derived from *L. peruvianum*, is called the Mi-1 allele. The susceptible allele from *L. esculentum*, is referred to as the wild type allele, and designated '+'. It is believed that all commercial tomato cultivars containing the Mi-1 resistance allele are derived from the interspecific hybrid created by Smith. Although homozygous Mi-1 lines were developed as early as 1949 (Frazier and Dennett, (1949) Proc. Am. Soc. Hort. Sci. 54:225-236), it was not until the mid-1970's that the Mi-1 allele began to be commonly used in commercial cultivars. Two developments led to this commercial implementation. First, Rick and Fobes reported a linkage between an isozyme marker called alkaline phosphatase (Aps) and the Mi locus ((1974) Tomato Genet Coop. Rep. 24:25). The early use of a molecular marker test allowed breeders to follow the trait without performing pathology testing. Second, hybrid tomato cultivars were becoming more accepted by commercial growers. Despite breeding with the Mi-1 allele for six decades, there remains today significant genetic drag associated with the Mi-1 introgression from *L. peruvianum*, including a localized necrotic response (Ho et al. (1992) The Plant Journal, 2:971), smaller fruits and less fruit set under stress conditions.

Breeders found that the Mi-1 allele was efficacious when present as a heterozygote, which allowed them to deliver the nematode resistance trait to the hybrid from only one parent. This in turn allowed breeders to largely overcome the genetic drag by using a second inbred parent that have *esculentum* genes in this region of chromosome 6. The creation of hybrid cultivars allowed for the implementation of this breeding strategy. The dominant Mi-1 allele was bred into one of the inbred parents, and the susceptible allele ('+') with surrounding *esculentum* alleles that allowed for masking most of the genetic drag were bred into the second inbred parent. That the genetic drag could be masked in the heterozygous condition provides indirect evidence that there are genes in this region of the genome that affect the general health of the plant, fruit size and fruit yield because of the ability to respectively mask the localized necrotic response, smaller fruit size and less fruit set under stress conditions.

Plant resistance genes have been shown to be clustered in the genome, and in tomato, are commonly found near the centromeres. The Mi locus is located in one of these disease resistance clusters, near the centromere on chromosome 6. In addition to having the Mi resistance locus, other resistance genes for geminiviruses, Oidium lycopersicum (van de Beek et al. (1994) Theoret. Appl. Genet. 89:467-473), and two resistance genes for Cladosporium fulvum races 2 and 5 (Dickinson et al. Mol. Plant Microbe Interact. (1993) 6:341-347) are all tightly linked genetically in this centromeric region of chromosome 6.

The difficulty of the Mi-1 introgression, even after many decades, has been the inability to reduce the genetic drag associated with the trait. Alternate explanations for this difficulty are that the Mi-1 resistance gene is pleiotropic, and contributes to the genetic drag directly, or that there is a suppression of recombination in this genomic region that limits the progress of genetic drag reduction. Various experimental approaches have addressed this question. Using a combination of genetics and cytogenetics, Zhong et al. ((1999) Theoret. Appl. Genet. 98:365-370) showed that, based on the genome size of tomato, the physical distance between the Mi locus and the Aps locus should be about 750,000 base pairs, based on the genetic estimation of ~1 cM of genetic distance. Their fluorescence in situ hybridization (FISH) results, however, showed that this physical distance is actually 40,000,000 base pairs. This discrepancy between the genetic and physical distances between these loci led Zhong et al. to predict that recombination around the Mi locus is reduced approximately 50-fold compared with the average for the genome. Kaloshian et al. ((1998) Mol. Gen. Genet. 257:376-385) took a comparative genetic approach, and showed that a L. peruvianum x L. peruvianum cross had 8-fold higher recombination in this region compared to the L. esculentum x L. peruvianum derived population. In addition to these experiments, it is well known that recombination is generally suppressed in centromeric regions. Milligan et al. (1998, Plant Cell 10: 1307-1320) used transgenic complementation to introduce the cloned Mi resistance gene into the susceptible cultivar Moneymaker. That no pleiotropic effects were observed in these complementation tests strongly suggests that the horticultural defects associated with the Mi introgression are due to genetic drag. These studies provided insight into the difficulty associated with introgressing disease resistance genes in this region of chromosome 6.

In 1998, Kaloshian et al. described a co-dominant, PCR-based molecular marker called REX-1, which was closer to the Mi locus than the Aps isozyme marker (Mol Gen Genet. 257:376-385). This DNA-based marker was rapidly adopted by tomato breeding programs, and greatly facilitated the development of new nematode resistance hybrid cultivars.

Although the tomato breeding community has rapidly disclosed its progress in introgressing the Mi-1 nematode resistance allele through scientific publications, the unlikelihood of success for this difficult breeding approach has been recognized by the USPTO in the issuance of several patents in this area (U.S. Pat. Nos. 6,414,226, 6,096,944, 5,866,764, and 6,639,132).

Reports of resistance to tomato yellow leaf curl geminivirus (TYLCV) have existed for nearly 40 years. Cohen first reported some tolerant genotypes as early as 1964 (Cohen and Harpaz (1964) Entomol. Exp. Appl. 7:155-166), then identified L. pimpinellifolium and L. peruvianum as containing higher levels of TYLCV resistance (Cohen and Nitzany (1966) Phytopathology 56:1127-1131). In the 1990's, Pilowski and Cohen reported tolerance from L. peruvianum (PI126935) with as many as five recessive genes (Plant Disease 74:248-250). Michelson et al. discovered ((1994) Phytopathology 84:928-933), and Hoogstraten (U.S. Pat. No. 6,414,226) later independently confirmed TYLCV resistance in L. chilense. This resistance locus is referred to as the Ty locus, and the resistance allele from L. chilense has been named Ty-1.

Like the Mi locus, the susceptible allele at the Ty locus is referred to as the wildtype, or '+'. Zamir et al. mapped the Ty locus to the centromeric region of chromosome 6 ((1994) Theoret. Appl. Genet. 88:141-146). The Ty-1 allele acts as a dominant allele, thus both lines that are fixed for the Ty-1 allele or that are heterozygous (Ty-1/'+') are resistant to TYLCV.

The inbred tomato line FDR16-2045, containing the Ty-1 resistance gene from L. chilense also confers resistance to nematodes because of a resistance gene from L. chilense that was also introgressed at the nearby Mi locus (Hoogstraten, U.S. Pat. No. 6,414,226). That these two resistance genes for nematodes and geminiviruses are co-inherited in line FDR16-2045 demonstrates that the Ty and Mi loci are closely positioned genetically. The nematode resistance allele at the Mi locus, as introgressed from L. chilense in line FDR16-2045 is referred to as Mi-J. Line FDR16-2045 is a valuable breeding inbred because it allows breeders to create commercial hybrids containing efficacious resistance alleles for nematodes and geminiviruses, with the ability to countermand most of the genetic drag by using a second inbred parent with the '+' type alleles at the Mi and Ty loci. The genetic drag from this introgression can be manifested as autonecrosis, longer internodes, smaller fruits and less fruit set under stress conditions.

However, through pathology testing it has been found that the Mi-J allele from L. chilense is not as effective as the Mi-1 allele from L. peruvianum. This is particularly evident when the Mi-J allele is paired in an F1 hybrid with the '+' susceptible allele at the Mi locus. Using molecular techniques, the present inventors were able to design molecular marker tests to distinguish the three possible alleles (Mi-1, Mi-J and '+') at the Mi locus.

Tomato breeders are faced therefore with a limitation in their ability to deliver multiple resistance genes that map to the centromeric region of chromosome 6 while retaining the ability to mask the genetic drag associated with these introgressions. To pyramid all the known resistance genes that map in this region of chromosome 6 in a hybrid cultivar, a breeder would have to have one parent with the introgression from L. peruvianum containing the nematode resistant gene Mi-1, another parent with the introgression from L. chilense containing the TYLCV resistance gene Ty-1, another parent with the introgression from L. hirsutum containing the resistance gene for Oidium, another parent with the introgression from L. pimpinellifolium containing the resistance genes for races of Cladosporium, and yet another parent containing the '+' type alleles from esculentum in order to mask the genetic drag associated with some of these introgressions. This task is impossible for the breeder because they have only two parent lines to choose from to make hybrid cultivars. This dilemma is also shown graphically by Ho et al. ((1992) The Plant Journal 2:971-982, see FIG. 6), and by Liharska et al. ((1996) Genome 39:485-491, see FIG. 1).

Thus, there remains a need to identify a recombinational event in this area of the genome known to have severely suppressed recombination, and that will contain the most efficacious allele for nematode resistance, Mi-1, originally introgressed from *L. peruvianum*, with the most efficacious allele for TYLCV resistance, Ty-1, originally introgressed from *L. chilense*. Tightly linked alleles juxtapositioned in this manner are said to be in the coupling phase, or in cis. Such a combination of efficacious resistance alleles in cis would allow tomato breeders to create tomato hybrids with the most efficacious resistance to TYLCV and nematodes, while retaining the freedom of having a second inbred parent to either mask the genetic drag, or deliver additional resistance genes, such as the resistance genes for *Oidium, Cladosporium*, or yet to be discovered resistance alleles in this disease cluster.

SUMMARY OF THE INVENTION

By the present invention is provided a *Lycopersicon esculentum* plant comprising within its genome at least one tomato yellow leaf curl virus (TYLCV) resistance allele and at least one root knot nematode resistance allele, characterized in that the resistance alleles are present in coupling phase at different loci on one chromosome and in that the plant is resistant to TYLCV and highly resistant to at least one root knot nematode species selected from the group consisting of *Meloidogyne arenaria, Meloidogyne incognita* and *Meloidogyne javanica*.

Also provided is a *Lycopersicon esculentum* plant comprising within its genome at least one tomato yellow leaf curl virus (TYLCV) resistance allele and at least one root knot nematode resistance allele, characterized in that said resistance alleles are present in coupling phase at different loci on one chromosome and in that said plant is resistant against both TYLCV and at least one root knot nematode species selected from *Meloidogyne arenaria, Meloidogyne incognita* and *Meloidogyne javanica*, wherein said root knot nematode resistance allele is not the Mi-J allele from *L. chilense*.

In one preferred embodiment, a plant of the invention having a root knot nematode resistance score of less than about 1.0 is provided, while in a further preferred embodiment a root knot nematode resistance score of less than about 0.5, more preferred less than about 0.25 and even more preferred less than about 0.05 is provided. In one embodiment the plant is a hybrid plant.

In one preferred embodiment the TYLCV resistance allele is the allele designated as Ty-1. In another preferred embodiment the root knot nematode resistance allele is the allele designated as Mi-1. In a further preferred embodiment the TYLCV resistance allele and the root knot nematode resistance allele are from *Lycopersicon chilense* and from *Lycopersicon peruvianum*, respectively.

Preferably, the TYLCV resistance allele and the root knot nematode resistance are non-transgenic.

In another aspect of the invention a fruit or a seed of such a *Lycopersicon esculentum* plant is provided.

The invention may provide an inbred commercial *Lycopersicon esculentum* plant, or, alternatively, a plant according to this invention may be used as parent in a cross with another *Lycopersicon esculentum* plant. The invention thus provides a hybrid *Lycopersicon esculentum* plant produced by the method of crossing a plant of the invention with an inbred plant lacking the TYLCV resistance allele and lacking the root knot nematode resistance allele.

In a preferred embodiment of this aspect of the invention, a hybrid *Lycopersicon esculentum* plant is provided where both of the TYLCV resistance allele and the root knot nematode resistance allele are heterozygous. More preferred is such a hybrid plant having good horticultural characteristics, and even more preferred is a hybrid plant having greatly reduced genetic drag normally associated with the wild tomato species introgressions providing the TYLCV resistance allele and the root knot nematode resistance allele.

Preferably, the hybrid plant shows greatly reduced genetic drag effects as are those associated with the wild species *Lycopersicon chilense*, and greatly reduced genetic drag effects as are associated with the wild species *Lycopersicon peruvianum*. More preferably, the hybrid plant presents greatly reduced genetic drag symptoms selected from the group of symptoms consisting of auto-necrosis, longer internodes, smaller fruit, less fruit set and horticulturally inferior plant architecture.

The loci of the TYLCV resistance allele and the root knot nematode resistance allele occur within the same disease resistance cluster on the chromosome. Thus, in an even more preferred embodiment of the invention, at least one additional disease resistance allele within the cluster is provided in the repulsion phase, or in trans to the Ty-1 TYLCV resistance allele and the Mi-1 root knot nematode resistance allele. In one alternative embodiment of this aspect of the invention, the additional disease resistance allele provides resistance to a disease selected from the group consisting of *Cladosporium* race 2, *Cladosporium* race 5 and *Oidium*.

BRIEF DESCRIPTION OF THE DRAWINGS

Various exemplary embodiments of this invention will be described in detail, with reference to the following figures, wherein:

FIG. 1 shows a comparison of the polynucleotide sequences of the marker locus near the Ty+ (SEQ ID NO: 11) and Ty-1 (SEQ ID NO: 10) alleles and the identification in the shaded boxes of 19 single nucleotide polymorphisms between the polynucleotide sequences. The circle identifies two (2) adjacent polymorphisms at base pairs 97-98 in the Ty-1 sequence and 96-97 in the Ty+ sequence, where a TaqI restriction enzyme recognition site occurs in the Ty-1 allele only.

FIG. 2 shows a comparison of the polynucleotide sequences of the marker locus near the Mi+, Mi-1, and Mi-J alleles and the identification in the shaded boxes of 20 single nucleotide polymorphisms between the polynucleotide sequences. The circles identify polymorphisms at base pairs 603 and 754.

DETAILED DESCRIPTION OF THE INVENTION

Figure 3:
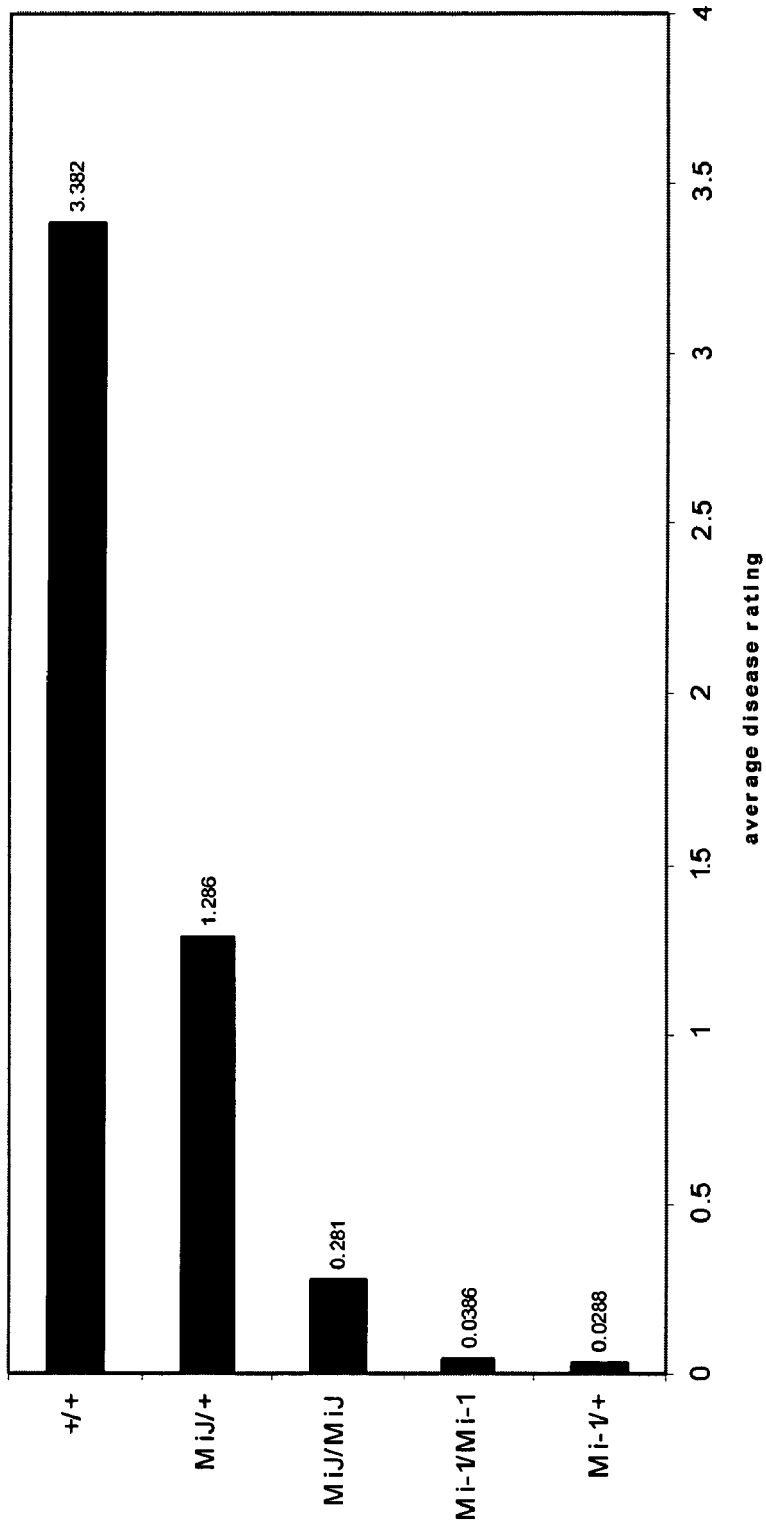
FIG. 3 shows the average nematode resistance rating of five plant genotypes, comprising various allele combinations at the Mi locus.

The present invention provides a tomato plant (*Lycopersicon esculentum*) produced from a recombinational event and having Mi-1, originally introgressed from *L. peruvianum*, in cis with Ty-1, originally introgressed from *L. chilense*.

Definitions

Botanical terminology: Linnaeus is considered the father of botanical classification. Although he first categorized the modern tomato as a Solanum, its scientific name for many years has been *Lycopersicon esculentum*. Similarly, the wild relatives of the modern tomato have been classified within the *Lycopersicon* genus, like *L. pennellii, L. hirsutum, L. peruvianum, L. chilense, L. parviflorum, L. chmielewskii, L. cheesmanii, L. cerasiforme*, and *L. pimpinellifolium*. Over the past few years, there has been debate among tomato researchers and botanists whether to reclassify the names of these species. The newly proposed scientific name for the modern tomato is Solanum lycopersicum. Similarly, the names of the wild species may be altered. *L. pennellii* may become *Solanum pennellii*, *L. hirsutum* may become *S. habrochaites*, *L. peruvianum* may be split into S. '*N. peruvianum*' and S. 'Callejon de Huayles', *S. peruvianum*, and *S. corneliomuelleri, L. parviflorum* may become *S. neorickii, L. chmeilewskii* may become *S. chmielewskii, L. chilense* may become *S. chilense, L. cheesmaniae* may become *S. cheesmaniae* or *S. galapagense*, and *L. pimpinellifolium* may become *S. pimpinellifolium* (Solanacea Genome Network (2005) Spooner and Knapp; http://www.sgn.cornell.edu/help/about/solantum_nomenclature.html).

Thus, although the names for tomato and its relatives may change, for the purpose of clarification, the modern tomato and its wild relatives are defined using the existing names that all fall within the *Lycopersicon* genus.

Nematodes: Root-knot nematodes (*Meloidogyne* spp.) are common in soil, and most have a wide host range, causing problems in many annual and perennial crops. Tomatoes are among the most seriously affected, with the nematode causing problems in all tomato growing areas. Root-knot nematodes are difficult to identify, and there are more than 50 species identified, though a few species (e.g. *M. javanica, M. incognita,* and *M. arenaria*) cause the majority of problems for tomato growers.

As used herein, the term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus.

As used herein, the term "locus" (loci plural) means a specific place or places or a site on a chromosome where for example a gene or genetic marker is found. The "Mi locus" refers herein to the location in the tomato genome at which one or more alleles are located, which determine the degree of root knot nematode resistance the plant or plant tissue has. The term "Ty locus" refers herein to the location in the tomato genome at which one or more alleles are located, which determine the degree of TYLCV resistance the plant or plant tissue has.

As used herein, the terms "in the coupling phase" and "in cis" refer to a genetic condition in which the alleles of two different loci occur together linked on one (homologous) chromosome. For example, when the alleles Ty-1 and Mi-1 are located on one chromosome homologue, these alleles are "in the coupling phase". In contrast, if the alleles Ty-1 and Mi-1 are located on different homologous chromosomes of a homologous pair, they are said to be "in the repulsion phase", or "in trans".

A "recombinant" or "recombinational event" refers herein to a plant having a new genetic make up arising as a result of crossing over and independent assortment of the homologous chromosomes.

A "TYLCV resistance allele" refers to an allele, which when present in the genome, confers "resistance" or "intermediate resistance" to tomato yellow leaf curl virus infection and/or damage. A plant or a plurality of plants are said to be "resistant" to TYLCV when the plants have an average disease score of between 0 and 1, or equal to 0 or 1, using the "TYLCV resistance assay" (see below). A plant or a plurality of plants are said to have "intermediate" TYLCV resistance when the plants have an average disease score of about 2, using the TYLCV resistance assay. Plants having an average disease score of about 3 or more are said to be susceptible.

A "root knot nematode resistance allele" refers to an allele, which when present in the genome confers resistance to at least one or more nematode species selected from *M. incognata, M. javanica* and *M. arenaria*. A plant or a plurality of plants are said to be "highly resistant" to at least one of these root knot nematode species when the plants have an average disease score of less than about 0.1, when using the "Root knot nematode resistance assay" (see below). For example Mi-1/Mi-1 plants and Mi-1/+ plants are highly resistant. A plant or a plurality of plants are said to have "intermediate resistance" when the plants have an average disease score of about 0.1 or more, but below 1.0 (for example plants with the alleles MiJ/MiJ). Plants having an average disease score of 1.0 or more but below 2.0 are said to have "moderate resistance" (for example plants with the alleles MiJ/+), while plants having an average disease score of 2.0 or more are said to be susceptible (for example plants with the alleles +/+).

A "TYLCV resistance assay" refers to a plurality of plants being grown in a field in which natural TYLCV infection occurs and scoring disease symptoms at one or more time points following infection using a scale of 0-4, as further described in the Examples, and determining the average disease rating for a plurality of plants having a specific allelic composition (genotype) at the Ty locus.

A "nematode resistance assay" refers to a plurality of plants being grown in soil inoculated with *M. incognita, M. javanica* or *M. arenaria* inoculum and scoring the root galls after about 28 days on a scale of 0-4, as further described in the Examples, and determining the average disease rating for a plurality of plants having a specific allelic composition (genotype) at the Mi locus.

As used herein, the term "heterozygous" means a genetic condition existing when two different alleles reside at a specific locus, but are positioned individually on corresponding pairs of homologous chromosomes in the cell of a diploid organism (e.g. Mi-1/+). Conversely, as used herein, the term "homozygous" means a genetic condition existing when two identical alleles reside at a specific locus, but are positioned individually on corresponding pairs of homologous chromosomes in the cell of a diploid organism (e.g. Mi-1/Mi-1).

As used herein, the term "plant" includes the whole plant or any parts or derivatives thereof, such as plant cells, plant protoplasts, plant cell tissue cultures from which tomato plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

A "molecular assay" (or test) refers to a (DNA based) assay that indicates (directly or indirectly) the presence or absence of a particular allele at the Mi or Ty locus. In addition it allows one to determine whether a particular allele is homozygous or heterozygous at the Ty or Mi locus in any individual plant. For example, in one embodiment a nucleic acid linked to the Mi or the Ty locus is amplified using PCR primers, the amplification product is digested enzymatically and, based on the electrophoretically resolved patterns of the amplification product, one can determine which Mi or Ty alleles are present in any individual plant and the zygosity of the allele at the Mi or Ty locus (i.e. the genotype at each locus). Examples are SCAR, CAPS and similar assays.

As used herein, the term "variety" or "cultivar" means a plant grouping within a single botanical taxon of the lowest known rank, which can be defined by the expression of the characteristics resulting from a given genotype or combination of genotypes.

As used herein, the term "wild type", means the naturally occurring allele found within *L. esculentum*. At the nematode resistance locus Mi, and the TYLCV locus Ty, these wild type alleles from *L. esculentum* confer susceptibility to these pathogens and are designated as Mi+ and Ty+ herein, or simply "+".

As used herein, the term "variant" or "polymorphic variant" refers to nucleic acid sequences that are essentially similar to a given nucleic acid sequence. For example, the term "variants thereof" or "variants of any of SEQ ID NO: 1-11" refers to a polynucleotide sequence having one or more (e.g. two, three, four, five or more) nucleotides deleted (deletion variants) from said polynucleotide sequence or having one or more nucleotides substituted (substitution variants) with other nucleotides or one or more nucleotides inserted into said polynucleotide sequence (insertion variants).

Variants of SEQ ID NO: 1-11 include any nucleotide sequences that are "essentially similar" to any of SEQ ID NOs: 1-11. Sequences which are essentially similar to SEQ ID NOs: 1-11 are nucleic acid sequences comprising at least about 90%, more preferably 91%, 92%, 93%, 94%, 95%, 96%, 97%, 98% or 99% or more nucleic acid sequence identity to one or more sequences of SEQ ID NOS: 1-11, when optimally aligned using, for example, the Needleman and Wunsch algorithm, with, for example, the programs GAP or BESTFIT using default parameters. GAP default parameters are a gap creation penalty=50 (nucleotides) and gap extension penalty=3 (nucleotides). For nucleotides the default scoring matrix used is nwsgapdna (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA or the open-source software Emboss for Windows (current version 2.7.1-07). Variants also include fragments or parts of any of these sequences.

Plants and Plant Parts According to the Invention

In one embodiment the present invention provides a tomato plant (*Lycopersicon esculentum*) comprising in its genome the Mi-1 allele, originally introgressed from *L. peruvianum*, in cis with the Ty-1, originally introgressed from *L. chilense*, as well as plant cells and tissues, seeds or fruit of such plants. These plants can be made, for example, by crossing publicly available commercial varieties, each comprising a (preferably fixed) allele of interest (here Mi-1 or Ty-1) and by selecting recombinant plants, comprising Mi-1 and Ty-1 in cis, from the F2 plants obtained from the cross, or from any further generation obtained by further selfing or crossing of the F1 (e.g. an F2 or backcross population). As the incidence of recombination is exceedingly low, requiring large numbers of events, the selection is preferably carried out using one or more Mi allele specific or allele discriminating molecular assays, such as SCAR or CAPS assays. For example, one or more of the three SCAR assays referred herein to as "SCAR assay for the Ty locus", "SCAR assay No. 1 for the Mi locus" and "SCAR assay No. 2 for the Mi Locus", as described in the Examples, may be used. In these assays 3 primer pairs are used in a PCR reaction (SEQ ID NOS: 1 and 2, SEQ ID NOS: 3 and 4 and SEQ ID NOS: 5 and 6), followed by an enzyme restriction and detection of the fragments obtained to detect polymorphisms between the PCR amplification products.

It is understood that routine experimentation can be used to develop a similar assay. For example "variants" of any of the primer sequences may be used, or primers or probes which hybridize to other parts of the genome near or on the Mi and Ty locus.

Plants comprising Mi-1 and Ty-1 in cis may be homozygous or heterozygous. These plants may be used in further crosses to transfer the alleles as a single unit to other tomato plants to generate, for example, hybrids or inbreds. In a preferred embodiment hybrid plants are provided that comprise the Mi-1 and Ty-1 alleles in coupling phase and susceptible, or Mi+ and Ty+, alleles on the homologous chromosome. These plants have the benefit of having significantly reduced or no genetic drag symptoms normally associated with the Mi-1 and Ty-1 alleles when these alleles are present in the homozygous condition.

Genetic drag symptoms refer to one or more symptoms selected from the group of auto-necrosis, longer internodes, smaller fruits, less fruit set and horticulturally inferior architecture, compared to a plant lacking the Mi-1 and Ty-1 alleles. Those skilled in the art will recognize that such symptoms of genetic drag will adversely affect the commercial acceptance of inbred or hybrid plant lines by growers. Generally, the presence of an adverse level of genetic drag can be determined by the presence of one or more of these symptoms to such a degree that the plant line becomes commercially unacceptable.

The tomato plants of this invention comprise an average nematode resistance score of less than about 0.25, preferably less than about 0.2, more preferably less than about 0.1 or less than about 0.05, such as 0.03 or 0.02. In addition, these plants are resistant to TYLCV and have an average TYLCV resistance score of lower than or equal to 1.0, as determined in the described assay.

Plants Comprising Other Nematode and TYLCV Resistance Alleles

In another embodiment the invention provides a method of making and/or selecting the above recombinant, as well as a method for making and/or selecting other recombinants having at least one Mi resistance allele and at least one TYLCV resistance allele in coupling phase (in cis), preferably chromosome 6 of *L. esculentum*. Such plants are characterized by having high, intermediate or moderate resistance to nematodes of the species *M. arenaria, M. incognita* and/or *M. javanica* and by having resistance or intermediate resistance to TYLCV, when using the resistance assays described herein. Also provided are recombination events made using this method, as well as tissues, cells, seeds and fruit of these plants and the use of any of these plants to generate hybrid or inbred plants comprising the Mi and Ty resistance alleles in cis. Plants comprising the Mi-J allele from *L. chilense* in coupling phase with the Ty-1 allele are, however, explicitly excluded, as such plants naturally occurred already accidentally in the prior art (U.S. Pat. No. 6,414,226), although they were not made according to the present invention. In any case, plants with the Mi-J allele from *L. chilense* in coupling phase with the Ty-1 allele do not show high level nematode resistance, i.e., are not highly resistant as defined herein. Thus, particularly preferred are plants conferring resistance to TYLCV and high resistance to nematodes.

In one embodiment the present invention relates to the making of a tomato plant that comprises an allele that confers resistance to TYLCV in the coupling phase with an allele that confers resistance to root-knot nematodes. The allele that confers resistance to TYLCV and the allele that encodes for resistance to root-knot nematodes may originally derive from different germplasm sources (i.e. different species of tomato), such as, but not limited to, *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon pennellii, Lycopersicon peruvianum, Lycopersicon chilense* or *Solanum lycopersicoides*.

Thus, in one embodiment a method for making a *Lycopersicon esculentum* plant comprising at least one TYLCV resistance allele and at least one root knot nematode resistance allele in the coupling phase at two loci is provided, wherein the method comprises the steps of: (a) crossing a *Lycopersicon* plant comprising a TYLCV resistance allele with a *Lycopersicon* plant comprising a root knot nematode resistance allele, (b) analysing progeny of said cross for the presence of the resistance alleles at each of the two loci using one or more molecular assays, and (c) selecting one or more plants comprising the resistance alleles in the coupling phase.

Resistance assays may be optionally performed at any stage of the method. A further optional step (d) comprises selfing the plant obtained or crossing the plant obtained with another tomato plant to create a hybrid plant. In a preferred embodiment the plant obtained by the method is resistant to TYLCV and highly resistant to nematodes (as defined).

The starting plants of step (a) can be selected using pathological tests as described in the Examples. They may be wild or cultivated plants, or modified plants, such as mutagenized or transformed plants. For example, approaches such as TILLING (Targeting Induced Local Lesions IN Genomics; McCallum et al., 2000, Nat Biotech 18:455, and McCallum et al. 2000, Plant Physiol. 123, 439-442) or ECOTILLING (Henikoff et al 2004, Plant Physiology Preview May 21, 2004) may be used to generate and/or select plants with modified pathogen resistance and/or mutations in alleles of the Ty or Mi locus. These plants may then be used as sources of Ty and Mi resistance alleles.

The progeny of the cross are then analyzed, using one or more molecular assays according to the invention (described below). The progeny analyzed and from which plants are selected may be any of various generations of progeny, such as the F2, F3 generation, etc., a backcross generation (BC1, BC2, etc) etc., depending on the crossing/selection scheme desired and the alleles present in the plants used. The molecular assay is preferably carried out on F2 plants. Also, progeny of different generations may be repeatedly tested using pathological assays and/or one or more molecular assays. Several molecular assays may be carried out in one generation, or one or more different assays may be carried out in different generations. Thus, steps (a), (b) and/or (c) may be repeated several times. The aim is to identify recombinants comprising the desired Ty and Mi resistance alleles in the coupling phase (step c). In this method any Ty resistance allele may be combined (in the coupling phase) with any Mi resistance allele.

The plants can be distinguished from other plants using molecular assays, based on, for example a nucleic acid sequence near or at the Ty- and near or at the Mi-locus. These analyses allow the allelic make up at these two loci to be determined. For example, a plant according to the invention comprises SEQ ID NO: 8, or a nucleic acid sequence essentially similar thereto (and indicative of an Mi resistance allele at the Mi locus), near the Mi locus and also SEQ ID NO: 10, or a nucleic acid sequence essentially similar thereto (and indicative of an Ty resistance allele at the linked Ty locus) near the Ty locus, whereby these regions are linked in coupling phase. Preferably one or more PCR based assays as described elsewhere herein are used to distinguish between different genotypes at the Mi and Ty loci and to select a recombinant plant having the desired alleles in coupling phase.

The selection of a recombinant plant comprising a Mi and a Ty resistance allele in the coupling phase and the introgression of this single Mendelian unit into other plants may be achieved using a combination of molecular biology, plant pathology and traditional breeding techniques. In a preferred approach, the present invention uses molecular biology techniques to discriminate between different alleles at the Ty and Mi loci to combine the desirable alleles for TYLCV resistance and root-knot nematode resistance into the genome of cultivated tomato in cis. The present invention facilitates the breeding of tomato hybrids with multiple resistance to both TYLCV and root-knot nematodes while enhancing the plant breeder's ability to mask the genetic drag that is typically associated with these traits, while retaining the freedom to combine the Ty and Mi resistance with resistance genes for *Oidium, Cladosporium* or yet to be discovered resistance genes present in this gene cluster.

By way of example, but not of limitation, the present invention provides for the development of tomato germplasm comprising any Ty resistance allele and any Mi resistance allele in the coupling phase, preferably as an in cis co-inherited unit located on chromosome 6. Once plants have been identified that have high levels of resistance, (e.g. comparable to resistance levels provided by Ty-1 and Mi-1), the nucleic acid regions disclosed herein, which are closely linked to the Mi and Ti loci, can be sequenced and the sequence information (of the linked marker region) used to develop a molecular assay for the alleles found in those plants. Alternative methods exist for identifying Mi or Ty resistance alleles in various germplasm, as will be apparent to those of skill in the art. Further details of such methods are provided below.

As mentioned previously, the present invention uses a combination of molecular biology, plant pathology and traditional breeding techniques. In one embodiment the molecular biology techniques used involve marker assays that employ for example nucleic acid primers which hybridize (and amplify) a nucleic acid region linked to the Mi and/or Ty locus, which will be discussed in more detail below. The present invention not only contemplates the specific assays disclosed in the Examples, which involve the Ty-1 and Mi-1 alleles, but any assays that can be developed and used to introgress into tomato any allele that encodes for resistance to TYLCV in the coupling phase with any allele that encodes for resistance to root-knot nematodes. For example, the present invention contemplates introgressing into tomato any variants (for example orthologs or evolutionarily diverged natural alleles or alleles generated by mutagenesis) of the Ty and/or Mi loci and the generation of plants comprising the alleles in cis.

Also provided herein are plants obtainable by any of the methods described and the use of those plants as parent in a cross with another *L. esculentum* plant. It should be noted that the present invention is in no way technically limited to one or more specific varieties of tomato, but is generally applicable to tomato plants (including inbreds, hybrids, etc.).

Molecular Assays According to the Invention

A number of molecular assays are provided herein which discriminate between the presence or absence of Ty-1 and Ty+ at the Ty-locus and between Mi-1, Mi-J and/or Mi+ at the Mi locus of a plant. One or more of these assays can be used in marker-assisted selection, i.e. to determine the allelic make up of plants at the Mi and Ty locus and to select plants having the desired Mi and Ty resistance alleles in coupling phase. Similar assays can be developed for any Mi and Ty resistance alleles, using routine molecular biology techniques. For example, any fragment of 10, 12, 14, 16, 18, 20, 21, 22, 23, 24, 25, 26, 30 or more consecutive nucleotides of SEQ ID NOS: 7-9 (or variant nucleic acid sequences) or of SEQ ID NOS. 10 or 11 (or variants thereof) may be used to design PCR primer pairs or, probes for nucleic acid hybridization and to develop discriminating molecular assays based on the nucleic acid information of the region amplified by such primer pairs or of the nucleic acid sequence to which such probes hybridize. The exact type of assay developed is not important, as long as it can discriminate between Mi resistance alleles and Ty resistance alleles and homozygosity/heterozygosity at the Mi and/or Ty locus. Examples of various types of assays are given below and in the Examples.

In order to perform the marker-assisted selection in the methods of the present invention, the subject tomato plants or plant parts are, for example, first subjected to DNA extraction, the techniques of which are known in the art (See Hnetkovsky et al., Crop Sci., 36(2): 393-400 (1996)). Once the extraction is complete, a molecular assay can be performed, including, but not limited to, a cleaved amplified polymorphic sequence (CAPS) assay (see Akopyanz et al., Nucleic Acid Research, 20:6221-6225 (1992) and Konieczny & Ausubel, The Plant Journal, 4:403-410 (1993)) or a SCAR assay. A SCAR assay involves amplifying DNA at the locus (e.g. a specific locus near the Ty locus or the Mi locus) by PCR followed by digestion with restriction enzymes. Polymorphisms between the nucleic acid sequences differentiates between different alleles (such as, but not limited to, the Mi+, Mi-J and/or Mi-1 alleles) by resulting for example in different sized restriction fragments.

Nucleic acid primers and enzymes are employed in these assays in order to identify which alleles are present at the Ty and/or Mi loci in the genome of a tomato plant, and, if said alleles are present, whether the alleles are present in a homozygous or heterozygous condition. The information obtained from both loci is used to identify those plants that have specific allelic combinations at the Ty and Mi loci in the coupling phase (i.e, in cis).

To create a marker-assisted selection test, one skilled in the art begins by comparing the DNA sequence from the donor source (i.e. the germplasm containing the disease resistance trait) with the corresponding DNA sequence from the recipient source (i.e. the germplasm containing the susceptible '+' alleles for the specific pathogen). Alternatively, a sequence comparison between DNAs from the donor and recipient can be performed at corresponding positions in the genome that are tightly linked genetically to the trait of interest. For the Ty and Mi loci, identification of polymorphisms near these traits are known in the art (See, Zamir et al., Theor. Appl. Genet. 88:141 (1994) and Williamson et al., Theor. Appl. Genet. 87:757 (1994)). For the Ty-1 allele, Zamir et al. found the restriction fragment length polymorphism (RFLP) TG97, which was originally mapped by Tanskley (Tanskley et al., Genetics 132:1141 (1992)) to be tightly linked to the Ty locus. Similarly, Williamson et al. found the REX-1 locus to be tightly associated with the Mi locus.

In one embodiment the molecular assay used is a SCAR assay, or several SCAR assays, as seen in the Examples. For example, SEQ ID NO: 10 provides the polynucleotide sequence near the Ty-1 allele from *L. chilense* LA1969. SEQ ID NO: 11 provides the polynucleotide sequences near the wild type Ty+ allele from *L. esculentum* at the TG97 locus. FIG. 1 shows a comparison of these sequences, highlighting several single nucleotide polymorphisms (SNPs) present between these two sequences. SNPs can be substitution mutants, insertions or deletions, which are commonly called INDELS. Using the polymorphisms between the alleles, those skilled in the art will recognize that any number of marker-assisted assays and primers (or probes) can be developed for the SNPs. Such an assay can be used to distinguish between the resistant Ty-1 allele from the susceptible Ty+ allele. For example, the primer pair of SEQ ID NOS: 1 and 2 amplifies a fragment of about 398 bp (using PCR amplification with e.g. genomic tomato DNA as template). Subsequent incubation of the amplification product with the enzyme TaqI (which recognizes and restricts the sequence T↓CGA) results in the restriction of the 398 bp product amplified from a plant comprising the Ty-1 allele into two nucleic acid fragments of about 95 bp and about 303 bp. A plant homozygous for Ty-1 will thus result in these two fragments (visualized e.g. as bands on a gel or otherwise), while a plant homozygous for the Ty+ allele will result in a single fragment of about 398 bp. A heterozygous plant (Ty-1/Ty+) produces all three fragments.

In a similar fashion, based on the data published by Williamson et al., Theoretical and Applied Genetics 87:757-763 (1994), the polynucleotide sequences of *L. esculentum, L. peruvianum* and *L. chilense* were determined at the locus nearby to Mi that is referred to as REX-1. These three polynucleotide sequences are provided in SEQ ID NOS: 7 (specific for Mi+), 8 (Mi-1) and 9 (Mi-J). A comparison of these polynucleotide sequences is shown in FIG. 2, which reveals 20 SNPs between these three sequences.

It is understood that the herein described SCAR assays can be easily modified or replaced by other molecular assays and can easily be developed for any allele of the Ty- and/or Mi- locus. Also, the assay may be based on other polymorphisms than SNPs, such as deletion, insertion or substitution of two or more nucleotides.

As already mentioned, specific or degenerate primers can be designed which hybridize to and amplify all or part of SEQ ID NOS: 7-11, or all or part of any variants thereof or flanking regions in the genome. Alternatively, the primers may be designed to amplify parts of the resistance alleles directly or other nucleic acid regions near the Mi- and Ty loci. Moreover, when desired, the primers of the present invention can be modified for use in other marker-assisted selection assays, such as, but not limited to, the TaqMan® assay from Applied Biosystems, Foster City, Calif., using techniques known in the art, including, but not limited to those described in U.S. Pat. Nos. 5,464,746, 5,424,414 and 4,948,882.

To design a new molecular test to distinguish a new Ty or Mi resistance allele, those skilled in the art recognize that one would, for example, first determine the DNA sequence at the marker locus on or near the Mi or Ty locus (using e.g. PCR amplification and the primer pairs described herein and sequencing of the amplification product), and then compare the sequence with the corresponding DNA of the other marker sequences (on or near other alleles of the Mi and Ty locus). With this DNA comparison, those skilled in the art could identify either new sequence polymorphisms or whether existing polymorphisms previously uncovered with other comparisons remain. Using these data, one can either design a new molecular test, or use an existing test to facilitate the selection of any allelic combination at the Ty and Mi loci together in cis.

Similar methods as those described above can be used to select and/or introgress an allele that encodes for resistance to root-knot nematodes. By way of an example, but not of limitation, an assay for determining the presence of the Mi-1 allele in the genome of a tomato plant will be described. An assay for determining the presence of the Mi-1 allele can be determined in a manner similar to those used to identify the Ty-1 allele described previously. However, if it is suspected that the plant under investigation might possibly contain the Mi-J allele, then the identification of the presence of the Mi-1 allele in the genome of the plant may, but will not necessarily, involve conducting two molecular assays, such as those described in the Examples. In any case, the order in which these assays are performed is not critical.

The above-described assays can be used individually and collectively in a breeding program to facilitate the breeding and/or selection of tomato plants that contain the Ty-resistance allele and the Mi resistance allele in the coupling phase.

One non-limiting example of how these methods can be used is described below, for the selection of a plant comprising Mi-1 and Ty-1 in coupling phase. A first inbred tomato line may be crossed with a second inbred tomato line to produce a hybrid plant. One tomato plant used in the cross contained the Ty-1 allele and the second plant the Mi-1 allele in its genome. A resulting plant (F1 hybrid) is then allowed to self-pollinate, fertilize and set seed (F2 seed). The F2 plants are grown from the F2 seed (or further selfed or crossed, e.g. backcrossed to one of the parents). These plants are then subjected to DNA extraction, the techniques of which are known in the art (See Hnetkovsky et al., 1996, Crop Sci., 36 (2): 393-400) and PCR is carried out directly on crushed tissue samples.

Thus, the above-described assays can be used to identify F2 plants (or other progeny) that contain the Ty-1 allele in a heterozygous state and the Mi-1 allele in a homozygous state. Alternatively, one can identify an F2 plant that contains the Ty-1 allele in a homozygous state and the Mi-1 allele in the heterozygous state. Thus, using one or more molecular assays, such as the SCAR assays described, recombinant plants can be identified which comprise Ty-1 and Mi-1 in coupling.

Because recombination between the Ty and Mi loci is low, finding recombinants in the F2 generation is rare. The assays described herein can also be used to determine if the Ty-1 and/or Mi-1 alleles are present in the genome of the plant in the homozygous or heterozygous condition. Depending upon the results of the assay(s), further breeding and molecular characterization may be necessary. For example, if the goal of the breeding program is to create an inbred line and the results of one or more of the above-described assays for a specific tomato plant being tested reveal that the plant contains the Mi-1 allele in its genome in a homozygous condition and the Ty-1 allele in a heterozygous condition, then that plant may be subjected to further self-fertilization, breeding and/or molecular characterization using one or more of the assays described herein, until it has been determined that said plant and its progeny, after selfing, contains both the Mi-1 allele and the Ty-1 allele in its genome under homozygous conditions. Once the Mi-1 and Ty-1 alleles are created in the coupling phase, or in cis, they will be inherited together. This heritable block of multiple resistance alleles provides the plant breeder with flexibility in creating new hybrids, while also allowing the plant breeder the ability to mask the genetic drag effects of the wild species introgressions with the second inbred parent. Also, easy combination with other resistance genes, such as *Oidium* and *Cladosporium* resistance genes is possible.

As mentioned briefly above, the methods of the present invention can be used to create new and superior inbred lines. These inbred lines can be used in subsequent breeding to create hybrid tomato plants that are resistant to TYLCV and root-knot nematodes and also possess other commercially desirable characteristics. Such inbred lines are useful in breeding because these lines allow for the transfer of the Ty-1 and Mi-1 alleles as a single co-inheritable unit that facilitates rapid breeding. Moreover, the above-described methods are also useful in confirming that an inbred line does in fact contain the Ty-1 allele and the Mi-1 allele in its genome in a homozygous condition and is maintaining its homozygosity. Once this confirmation is obtained, the inbred line can be used in crosses with a second inbred line to transfer the Ty-1 allele and Mi-1 allele to a hybrid tomato plant as a single co-inheritable unit. The second inbred line can carry the wild type alleles Ty+ and Mi+ to mask the effects of genetic drag.

Kits According to the Invention

In yet a further embodiment, molecular assays for determining the allelic composition at the Mi and/or Ty locus are provided. Such assays involve extracting DNA from one or more tomato plants, amplifying part of the DNA linked to or on the Mi and/or Ty locus using at least one PCR primer pair, optionally restriction the amplification product with one or more restriction enzymes, and visualizing the DNA fragments.

Further provided is a detection kit for determining the allelic make up of a plant or plant tissue at the Mi locus and at the Ty locus. Such a kit comprises one or more primer pairs, such as SEQ ID NO: 1 and 2, SEQ ID NO: 3 and 4 and/or SEQ ID NO: 5 and 6, or variants thereof. Further, instructions and optionally plant material or DNA (e.g. of control tissue) may be included.

EXAMPLES

Efficacy Evaluation for Nematode Resistance

Line FDR16-2045 is the subject of U.S. Pat. No. 6,414,226. It contains the Ty-1 allele at the Ty locus; the origin of this allele was an introgression from the *L. chilense*, a wild relative of the modern tomato, *L. esculentum*. The Ty-1 allele confers resistance to the commercially important pathogen, tomato yellow leaf curl virus (TYLCV). Co-inherited with this introgression, line FDR16-2045 contains the Mi-J allele at the nearby Mi locus. The Mi-J allele confers resistance to root knot nematodes, another commercially important pathogen. In breeding and pathology experiments the level of resistance conferred by the Mi-J allele is not as efficacious against root knot nematodes as was an alternate allele, Mi-1, at the Mi locus. This was particularly apparent when the Mi-J allele was present in a heterozygous condition, paired with the '+'—type susceptible allele from *L. esculentum*. Therefore, a series of pathology experiments described herein quantify the resistance levels using the Mi-1 and Mi-J resistance alleles.

Example 1

Pathology Testing for Determining Resistance to *Meloidogyne incognita*

A live pathogen assay was used to assess resistance to the *Meloidogyne incognita*, an etiological agent of root knot nematode disease in tomatoes. The resistance rating is based on the extent and size of gall formation. Table 1 provides the rating scoring system for determining root knot nematode resistance. A scale of zero to four was used (Table 1) to score for disease symptoms of *M. incognita*.

TABLE 1

| RATING SCORE | SEVERITY OF SYMPTOMS |
|---|---|
| 0 | NO GALLS PRESENT |
| 1 | ONE TO TWO SMALL GALLS (<1 MM) |
| 2 | SOME GALLS (3-7), SMALL IN SIZE (<1 MM), DISSEMINATED |
| 3 | SEVERAL GALLS (>7), BIGGER IN SIZE (>1 MM), DISSEMINATED |
| 4 | MANY GALLS, IN CHAINS, DEFORMED ROOTS |

*Meloidogyne incognita* inoculum was prepared by infecting plants from a susceptible tomato line for two months; at this time, the roots of the infected plants show mature egg masses from the pathogen. Roots were harvested for inoculum preparation and cut into four to five centimeter pieces. The test germinates seeds in the presence of infected inoculum. The seeds are sown into greenhouse benches containing a soil mixture of peat vermiculite and sand (4:1:1 ratio, respectively). Seeds from a line were sown in rows, approximately 4 cm apart, with 4.5 to 5 cm between the rows. Small holes were made, at approximate 12 cm intervals between each row, for the inoculum. Into these holes, two or three pieces of the prepared inoculum were inserted and covered with soil. With alternating spacing of the inoculum on each side of a row, each seed was approximately 6-7 cm from the inoculum. The seedlings were germinated and grown in a greenhouse with a daily temperature range between 22-26° C. The ratings were performed 28 days after sowing by pulling up each plant and inspecting the roots for the presence of galls.

Tests were performed in duplicate with breeding lines, hybrids and control lines. The results for pathology testing for nematode resistance are displayed in Table 2.

Because there are 14 samples, with varying genotypes at the Ty and Mi loci, performance trends in Table 2 may be difficult to recognize. Of the 14 samples, there are only five genotypes at the Mi locus. One genotype is homozygous for the susceptible allele from L. esculentum. This is designated +/+. A second genotype is a heterozygote, with the Mi-J allele paired with the susceptible '+' allele. A third genotype has the Mi-J allele in the homozygous state. The fourth and fifth genotypes contain the Mi-1 allele, present as a homozygote and as a heterozygote with the '+' allele, respectively.

When data in Table 2 are condensed and averaged according to the genotype at the Mi locus, the efficacy of different allelic combinations for nematode resistance become clear (FIG. 3). In FIG. 3, the average disease ratings for genotypes found in Table 2 are provided. Lines in Table 2 were parsed according to the genotypes at the Mi locus. These genotypic classes are shown on the Y axis. The X axis provides the average disease ratings for these five genotypic classes.

TABLE 2

| Pedigree code | Genotype | Mar. 24, 2003 | | | | | May 13, 2003 | | | | | Total | | | | |
|---|---|---|---|---|---|---|---|---|---|---|---|---|---|---|---|---|
| | | 0 | 1 | 2 | 3 | 4 | 0 | 1 | 2 | 3 | 4 | 0 | 1 | 2 | 3 | 4 |
| Breeding Lines | | | | | | | | | | | | | | | | |
| 97.5281.M.20.M.1.1 | Ty-1/Ty-1 Mi-1/Mi-1 | 10 | 1 | | | | 15 | 6 | | | | 25 | 7 | | | |
| 97.5281.M.251.M.1.1 | Ty-1/Ty-1 Mi-1/Mi-1 | 25 | | | | | 66 | | | | | 91 | | | | |
| 97.5281.M.251.M.2.1 | Ty-1/Ty-1 Mi-1/Mi-1 | 27 | | | | | 53 | | | | | 80 | | | | |
| FDR 16-2045 | Ty-1/Ty-1 Mi-J/Mi-J | 59 | 13 | 1 | 1 | | 47 | 8 | 6 | | | 106 | 21 | 7 | 1 | |
| Hybrids | | | | | | | | | | | | | | | | |
| Super Red[1] | Ty-1/Ty+ Mi-J/Mi+ | 11 | 2 | 6 | 1 | | 11 | 15 | 7 | 10 | 2 | 22 | 17 | 13 | 11 | 2 |
| Sadiq[2] | Ty-1/Ty+ Mi-J/Mi+ | 20 | 5 | 2 | | | 16 | 13 | 6 | 27 | | 36 | 18 | 8 | 27 | |
| Margo[3] | Ty-1/Ty+ Mi-J/Mi+ | 6 | 3 | 8 | | | 15 | 26 | 9 | 13 | | 21 | 29 | 17 | 13 | |
| 01C041 | Ty-1/Ty+ Mi-1/Mi+ | 25 | | | | | 28 | 1 | | | | 53 | 1 | | | |
| 01C043 | Ty-1/Ty+ Mi-1/Mi+ | 23 | | | | | 30 | | | | | 53 | | | | |
| 01C044 | Ty-1/Ty+ Mi-1/Mi+ | 24 | | | | | 39 | | | | | 63 | | | | |
| 01C046 | Ty-1/Ty+ Mi-1/Mi+ | 23 | | | | | 45 | 2 | | | | 68 | 2 | | | |
| Controls | | | | | | | | | | | | | | | | |
| Marmande verte[4] | Ty+/Ty+ Mi+/Mi+ | | | 7 | 11 | 20 | | | | 30 | 21 | | | 7 | 41 | 41 |
| 1047 | Ty+/Ty+ Mi-1/Mi-1 | 28 | 2 | | | | 27 | 1 | | | | 55 | 3 | | | |
| 99T6 | Ty+/Ty+ Mi-1/Mi+ | 51 | | 2 | 2 | | 17 | 2 | | | | 68 | 2 | 2 | | |

[1]Super Red is a commercially available Lycopersicon esculentum variety that is available in the Middle East and is sold by the Assignee of the present invention, Seminis Vegetable Seeds, Inc.
[2]Sadiq is a commercially available Lycopersicon esculentum variety that is available in the Middle East and is sold by the Assignee of the present invention, Seminis Vegetable Seeds, Inc.
[3]Margo is a commercially available Lycopersicon esculentum variety that is available in the Middle East and is sold by the Assignee of the present invention, Seminis Vegetable Seeds, Inc.
[4]Marmande Verte is an anthocyanin-less variety which is a mutant of the publicly known variety Marmande listed in the Community Variety Catalogue of the European Community (Publication Journal of the EU, C167A).

In the left hand column are the names of the lines tested. These are organized into sections containing breeding lines, hybrid lines and control lines. In the next column the genotypes at the Mi and Ty loci are listed. These genotypes were determined by molecular marker tests described herein. The next series of five columns contain the rating scores for tests scored on two separate occasions. The final five columns sum the results of these two tests.

FIG. 3 shows that the Mi-1 allele, originally introgressed from L. peruvianum, confers the strongest level of resistance to nematodes. It is also clear that the resistance is strong irrespective of whether the Mi-1 is present as a heterozygote (with the susceptible '+' allele) or as a homozygote. This demonstrates that the Mi-1 allele confers resistance in a dominant fashion. Compared with the other genotypes, the genotypes Mi-1/Mi-1 and Mi-1/+ confer a highly resistant phenotype for nematode resistance. This "highly resistant" class is defined as having an average resistance score, determined by the methodology described herein, of below 0.1.

The next most resistant class is from lines having the Mi-J allele, introgressed from *L. chilense*, in the homozygous state. This class of resistance is defined as "intermediate resistance", and is within the average scoring range of equal to or above 0.1, but below 1.0. Inbred line FDR16-2045 is therefore scored as having an intermediate level of resistance.

A third resistance class, defined as "moderate resistance", is exemplified by lines having the Mi-J allele in the heterozygous condition, paired with the susceptible allele, '+'. This class has an average resistance rating of greater than or equal to 1.0 but less than 2.0. If inbred line FDR16-2045 is used as an inbred parent to create a hybrid cultivar, and if the second parent contains the susceptible '+' allele, then that hybrid would show only modest resistance. When comparing the performance of the Mi-J allele in the intermediate resistant and modest resistant class, it is apparent that this gene acts in a semidominant fashion.

The final class is defined as susceptible, and contains those lines that are homozygous for the susceptible allele from *L. esculentum*, or +/+. This susceptible class is defined as having an average disease rating score of above 2.

These test results show the different levels of resistance that can be achieved in tomato breeding using the alleles from *L. peruvianum* (Mi-1), *L. chilense* (Mi-J) and *L. esculentum* ('+'). Based on these data, a tomato breeder can create a hybrid cultivar by crossing an inbred line containing the resistance allele at the Ty locus (Ty-1) with an inbred line containing the best resistance allele at the Mi locus (Mi-1). This strategy has two critical limitations, however. First, it eliminates the ability of the breeder to deliver other disease resistance genes that map to the disease cluster in the centromeric region of chromosome 6. Examples of other disease resistance genes known to map in this area are the *Cladosporium* resistance genes, race 2 and race 5, and the resistance gene for *Oidium*. Second, because the breeder is introgressing two regions each originating from a wild species, and each known to result in genetic drag, this limits his or her ability to mask the effects of the genetic drag by using genes from the modern tomato (*L. esculentum*).

The Ty-1 and Mi-1 in cis tomato plants described herein provide a novel combination of alleles that can address these limitations, and allow tomato breeders more choices for creating cultivars with multiple disease resistances.

Example 2

Protocol for Determining Resistance to Tomato Yellow Leaf Curl Virus (TYLCV)

This example describes a protocol for determining whether tomato plants are resistant, intermediate resistant or susceptible to TYLCV.

Plants are grown in a field with natural infection of TYLCV through *Bemisia tabaci*. Naturally occurring field infection is a preferred method of determining resistance in areas where the virus is endemic, as the movement of the viral pathogen can be controlled by various governmental agencies (quarantine disease). For example, the United States Department of Agriculture will not normally allow the introduction of the TYLCV pathogen into most tomato growing regions of the United States where the pathogen does not normally exist. Conducting disease screens under controlled conditions is cumbersome because of the need to raise the insects (*Bemisia tabaci*) for the transmission of the virus.

A scale of 0 to 4 was used (Table 3) to score for disease symptoms of TYLCV:

TABLE 3

| Rating score | Severity of symptoms |
| --- | --- |
| 0 | no symptoms |
| 1 | slight yellowing of leaves |
| 2 | clear yellowing symptoms on leaves with leaf curl |
| 3 | Stunted plants with severe symptoms of yellowing of leaves and leaf curl |
| 4 | Severely stunted plants with small yellowing curled leaves |

A plant line or variety is rated as resistant to TYLCV when the average score is 0-1, intermediate resistant when the average score is approximately 2 and susceptible when the average score is above 3. Alternatively, protocols for determining TYLCV that are known in the art can also be used. "Tomato Yellow Leaf Curl Virus from Sardinia is a whitefly-transmitted monopartite geminivirus"; A. Keyyr-Pour, M. Bendahmane, V. Matzeit, G. P. Acotto, S. Crespi, B. Gronenborn.; Nucleic Acids Research, Volume 19, p. 6763-6769.; Tomato Yellow Leaf Curl Virus: a whitefly transmitted geminivirus with a single genomic component", N. Navot, E. Pichersky, M. Zeidan, D. Zamir, H. Czosnek. Virology, 185, 1991, p. 151-161.

Molecular Tests to Discriminate Allelic Compositions at the Mi and Ty Loci.

A combination of three molecular marker tests was used to determine the genotypes at the Mi and Ty loci. At the Ty locus, only a single codominant molecular marker test is required to discern between the two alternate alleles possible, Ty-1 and '+'. Those skilled in the art will recognize codominant assays as being defined as tests that can discern all three allelic possibilities at bi-allelic loci. At these loci, three genotypes can be scored—each of the homozygous classes, and the heterozygous class. Typically, marker assays like sequenced characterized amplified regions, or SCAR assays, cleaved amplified polymorphic sites, or CAPS assay, and single nucleotide polymorphic, or SNP assays are all typically codominant assays. In contrast, random amplification of polymorphic DNA, and amplified fragment-length polymorphism (AFLP), are typically dominant markers, and do not provide as much information as codominant markers. At the Mi locus, two tests are required to determine the possible combinations between the three alleles (Mi-1, Mi-J and '+'). Although in no way limiting, the marker assays described herein are all SCAR-type assays.

Like most other molecular marker tests, the SCAR assays performed use the polymerase chain reaction, or PCR, which can amplify DNA around one billion-fold from very small amounts of starting material. The use of PCR is well known to those skilled in the art, and allows the researcher to only harvest very small amounts of plant sample in order to perform the test. Less than 1 $cm^2$ of leaf material, preferably young actively growing tissue, is needed to perform these tests. This is such a small sample that these marker tests are usually referred to as non-destructive. They are considered non-destructive as the taking of the sample does not interfere whatsoever in the way the plant develops. Thus, this small sample does not affect the outcome of any number of subsequent tests, from pathology testing, fruit biochemical analysis, yield trialing, or horticultural evaluations. In addition to being non-destructive, a SCAR assay also provides the additional advantage of time. Typically, the genotype at the locus or loci of interest can be ascertaining within 24 hours.

Each of the three molecular marker tests used requires the isolation of genomic DNA.

Example 3

Isolation of Tomato DNA for Marker Tests

By no way limiting, the following protocol can be used to extract tomato DNA for subsequent molecular marker testing. Those skilled in the art recognize that many DNA extraction protocols are available in the prior art. All chemicals described in the protocol can be obtained from Sigma Chemical Company, Saint Louis, Mo. The procedure involves the following steps:

1. Collect a plant part that is approximately the size of a well in the 96 well microtiter plate format. Preferably, either a seed sample is used, or a tissue sample is taken from young leaves.
2. Add 150 µl extraction buffer (200 mM Tris-HCl, pH 7.5; 250 mM NaCl; 25 mM EDTA; 0.5% SDS) to the sample and macerate the tissue.
3. Centrifuge the plate for 15 minutes at 1900-×g at 15° C.
4. Transfer 100 µl of the supernatant fraction to a new 96 well plate that contains 100 µl of 2.5M potassium acetate (pH 6.5) in each well. Mix by shaking for approximately 2 minutes at 200 rpm.
5. Centrifuge the plate for 15 minutes at 1900-x g at 15° C.
6. Transfer 75 µl of the supernatant fraction to a new 96 well plate containing 75 µl isopropanol. Mix, then shake for 2 minutes at 200 rpm.
7. Centrifuge the plate for 15 minutes at 1900-×g at 15° C.
8. Remove supernatant fraction and add 200 µl 70% ethanol to the pellet fraction. Shake at 200 rpm for 5 minutes, and then incubate overnight at −20° C.
9. Centrifuge the plate for 15 minutes at 1900-×g at 15° C.
10. Remove supernatant fraction. Add 200 µl of 70% ethanol to the pellet, allowing the alcohol to wash the pellet for 1 hour at room temperature.
11. Centrifuge the plate for 15 minutes at 1900-×g at 15° C.
12. Discard the supernatant fraction and dry the pellet fraction at room temperature. This takes about 1 hour.
13. Dissolve the pellet fraction in 100 µl TE (10 mM Tris, pH 8.0, 1 mM EDTA, 5 µg/ml RNAase A) for 15 minutes at 37° C. Unless proceeding to the PCR step, the DNA can be stored at 4° C. or −20° C.

Example 4

General PCR Conditions for the SCAR Assays

Each of the three SCAR marker assays shares a similar design and execution. Each assay contains a pair of specific DNA oligonucleotides, referred to as primers because these will be used in the PCR reaction to prime DNA synthesis. These primers are typically between 15 and 25 nucleotides in length; these stretches of nucleotides match the DNA sequence of the substrate at the marker locus to be amplified. These primers are designed such that they will facilitate the synthesis of an amplicon typically between 100 to 1,000 base pairs. Those skilled in the art know how to design these primers to create SCAR-type assays, and often use software programs, like the publicly available Primer 3 software (Whitehead Institute, Cambridge, Mass.) to assist in the design. Primers can be synthesized using methodology known in the art, or purchased from any number of custom oligonucleotide companies. All primers used in these assays were purchased from the Operon Company, Alameda, Calif. Other reagents in the PCR reaction can be purchased from any number of commercial suppliers; in the assays described herein, we purchased the four deoxyribonucleotide-5' triphosphates (dNTPs) from the Pharmacia Company, Kalamazoo, Mich., the PCR buffer and the Taq polymerase enzyme from the Applied Biosystems Company, Foster City, Calif. Those skilled in the art recognize that there is some flexibility in performing SCAR assays because there are many types of PCR machines and assay conditions that can be used. A model 9700 PCR machine from the Applied Biosystems Company, Foster City, Calif., was used with the following run parameters for each of the three assays. An initial denaturation step for 2 minutes at 94 C was followed by 35 cycles of amplification. Each amplification cycle had three steps of 30 seconds at 92 C, then 30 seconds at 50 C, then 90 seconds at 72 C. After the $35^{th}$ cycle, the samples were held at 72 C for 5 minutes. Although this ends the PCR amplification assay, the PCR machines were programmed to hold the finished reactions at 25 C until retrieved by the researcher.

Those skilled in the art recognize that there is considerable flexibility allowed in the PCR assay conditions. PCR reactions were prepared with 1 µL of the DNA template, 10 picomoles each of the two assay-specific PCR primers, a final volume of 200 µM for each of the four dNTPs, 2.5 µl, of 10×PCR buffer, and 1.25 units of Taq polymerase. Sterile water was used to bring the final volume of the reactions to 25 µL.

Each SCAR assay also has commonality in how the polymorphisms are revealed after the PCR reactions have been completed. For each test, the amplified region of DNA from the PCR reaction may contain a polymorphic restriction enzyme recognition site. Alternate alleles either have, or do not have this recognition site. When the PCR products are digested with a specific restriction enzyme, the amplicon is either not cut because the restriction enzyme site is not present, or digested asymmetrically into two fragments. The genotype of the locus can be determined by electrophoretically resolving these fragments on an agarose gel, staining the gel with ethidium bromide, which is a stain that binds DNA, then visualizing the fragments by exciting the DNA with ultraviolet light. The fragment sizes from the PCR reactions are determined by comparing them to known size standards, which are electrophoresed in nearby lanes in the agarose gel. Two of the SCAR assays use the restriction enzyme TaqI to reveal the polymorphisms. For these assays, 3 µL of 10× restriction enzyme buffer, 0.25 µL of TaqI restriction enzyme and 1.75 µL of water are added to the post-PCR reaction, and incubated at 65 C for approximately 3 hours. The third assay uses the restriction enzyme NlaIII to reveal the genotypes. In this test, 3.5 µL of 10× restriction enzyme buffer, 0.25 µL of NlaIII and 6.25 µL of water are added to the post-PCR reaction, and then incubated at 37 C for approximately 3 hours. Those skilled in the art recognize that restriction enzymes and buffers are sold by a number of commercial vendors. We used reagents from New Englands Biolabs, Beverly, Mass. After digestion with the restriction enzymes, the products were electrophoretically resolved on between 1-2% (w/v) agarose gels, according to methods well known in the art (*Current protocols in molecular biology* (1994) F. Ausubel, editor, John Wiley and Sons, New York).

Example 5

SCAR Test at the Ty Locus

Zamir mapped the Ty-1 gene close to a restriction fragment length polymorphism (RFLP) marker called TG97 ((1994)

Theoret. Appl. Genet. 88:141-146). Because RFLP assays are more difficult to perform, are destructive to the plant, costly, and slow to perform, this RFLP was converted to a SCAR marker by sequencing the RFLP locus using both the '+' allele and the resistance allele Ty-1 as substrates. Comparison of these sequences allowed for the discovery of the polymorphic restriction site.

The SCAR test is performed as described herein, with the following specific primer pairs.

```
SEQ ID 1:  5' TAA TCC GTC GTT ACC TCT CCT T 3'
and
SEQ ID 2:  5' CGG ATG ACT TCA ATA GCA ATG A 3'.
```

The polymorphism can be revealed by post-PCR digestion with the restriction enzyme TaqI. If the Ty-1 allele is present as a homozygote, the 398 base pair PCR amplicon will be digested into 95 and 303 base pair fragments because the amplicon produced from this allele contains the TaqI restriction recognition site. If the '+' type allele is present as a homozygote, the 398 base pair PCR amplicon will not be digested by the TaqI enzyme. For heterozygous samples, approximately half the PCR reaction will be digested into 95 and 303 base pair fragments and approximately half the PCR reaction will not be digested. When resolved electrophoretically, heterozygotes will have three fragments—95, 303 and 398 base pairs in length. In this manner, the genotype at the Ty locus can be rapidly and accurately determined.

Example 6

SCAR Test1 at the Mi Locus (Discriminating the Mi-1 or Mi-J Alleles from the '+' Allele)

Based on the data published by Williamson et al. (Theoretical and Applied Genetics 87:757-763 (1994)), the polynucleotide sequences of *L. esculentum, L. peruvianum* and L. were determined at the locus nearby to Mi that is referred to as REX-1.

The SCAR test is performed as described herein (also as described by Williamson et al.), with the following specific primer pairs.

```
SEQ ID 3:  5' AAC CGT GGA CTT TGC TTT GAC T 3'
and
SEQ ID 4:  5' TAA GAA CAG GGA CTC AGA GGA TGA 3'.
```

Like the SCAR assay described herein for the Ty locus, the Mi locus SCAR assay #1 also uses a polymorphic TaqI restriction enzyme recognition site; the polymorphism can be revealed by enzymatic digestion of the PCR products with the restriction enzyme TaqI. If the Mi-1 allele or the Mi-J allele is present as a homozygote, or the Mi-1 allele and Mi-J alleles are present as a heterozygote, the 595 base pair PCR amplicon will be digested into 145 and 450 base pair fragments because these alleles contains the TaqI restriction recognition site. If the '+' type allele is present as a homozygote, the 595 base pair PCR amplicon will not be digested by the TaqI enzyme. For heterozygous samples (Mi-1/+ or Mi-J/+, approximately half the PCR reaction will be digested into 145 and 450 base pair fragments and approximately half the PCR reaction will not be digested. When resolved electrophoretically, these heterozygotes will have three fragments—145, 450 and 595 base pairs in length. In this manner, one can determine whether the resistance alleles (either Mi-1 or Mi-J) are present or whether the susceptible allele ('+') is present, or whether the resistance alleles (either Mi-1 or Mi-J) and the susceptible allele ('+') are present as a heterozygote.

Example 7

SCAR Test2 at the Mi Locus (Discriminating the Mi-J from the Mi-1 or '+' Alleles)

Because the SCAR test described in example 5 above does not allow discrimination between the Mi-1 and Mi-J resistance alleles, another SCAR assay was developed at the REX-1 marker. This test was developed by sequencing the Mi-1, Mi-J and '+' alleles at this marker loci. Unfortunately, there wasn't a single nucleotide that had a different polymorphism for each of the three alleles. A single base polymorphism was discovered in a restriction enzyme recognition site called NlaIII. Specifically, the Mi-J allele contained this recognition site, while the Mi-1 and '+' alleles did not contain this recognition site.

Based on this polymorphism, a second SCAR assay was developed, and can be performed as described herein with the following specific primer pairs:

```
SEQ ID 5:   5' CTA CGG AGG ATG CAA ATA GAA
SEQ ID 6:   5' AAT CAT TAT TGT CAC ACT TCC CC
```

Following the PCR reaction, the polymorphism can be revealed by digesting the reaction with the restriction enzyme NlaIII by methods described herein. If the Mi-J allele is present, the 282 base pair amplicon will be digested into 124 and 158 base pair fragments. If either the Mi-1 allele, or the '+' allele are present, the amplicon is not digested by the NlaIII enzyme. Heterozygotes (either Mi-J/Mi-1 or Mi-J/+) will have all three fragments (124, 158 and 282 base pairs). Using both SCAR assays at the Mi loci (examples 5 and 6), the genotype at the Mi locus can be determined, irrespective of which combination of the three possible alleles are present (Mi-1, Mi-J or '+').

Example 8

Breeding Protocol to Combine the Most Efficacious Alleles at the Mi and Ty Loci

Starting with two parental lines, each containing a fixed allele of interest that are closely linked, those skilled in the art will recognize that there are several genetic strategies possible to achieve the goal of combining these traits of interest in cis. All of these strategies, however, begin by crossing the parental lines, each containing a trait of interest to make an F1 hybrid. Preferably, the parental lines should each be fixed for one of the traits of interest. The F1 plant can either be self pollinated to create a segregating F2 population, or it can be backcrossed to either parental line. Irrespective of the crossing strategy, those skilled in the art will recognize that novel recombinants of interest can be created as the F1 plant produces gametes through the process of meiosis.

By no means limiting, an F2 strategy was followed to combine the Mi-1 and Ty-1 alleles in cis. Specifically, a cross between inbred breeding lines FIR16-176 and FDR16-2045 was made in Nimes, France in the fall of 1997. Both of these breeding lines are from the tomato breeding program of Seminis Vegetable Seeds, Inc., the assignee of the present invention. Inbred line FIR16-176 contains the susceptible allele '+' at the Ty locus, and the Mi-1 allele at the nearby Mi locus. Inbred line FDR16-2045, which is the subject of U.S. Pat. No. 6,414,226, contains the Ty-1 allele at the Ty locus and the Mi-J allele at the nearby Mi locus. The F1 plant, designated #1652817, thus contains a pair of in cis pairings of alleles at the Ty and Mi loci, representing the parental genotypes. These pairings are commonly drawn underlined together, the underlining representing that the loci are genetically linked. For example, the F1 plant has the '+' Mi-1 and Ty-1 Mi-J in cis pairings. Although recombination could have occurred when the parentals underwent meiosis, no effective recombination could have occurred because each of these lines was fixed at the Mi and Ty loci.

F1 plant #1652817 was self-pollinated to create an F2 population. As the F1 plant created gametes through meiosis, most of the gametes retain the allelic combinations from the original parentals ('+' Mi-1 and Ty-1 Mi-J). The genetic distance between the Ty and Mi loci determines the relative frequency that the recombinant gametes ('+' Mi-J and Ty-1 Mi-1) will be produced. Because the Ty and Mi loci are closely positioned and numerous researchers have shown that recombination is suppressed in this region of chromosome 6, those skilled in the art would expect that the number of recombinant gametes would be very low compared with the parental gametes.

A series of molecular tests was then developed, described herein, to identify recombinants having the Ty-1 and Mi-1 alleles in cis, because identifying this in cis pairing through phenotypic pathology screening was not possible without multi-year, multi-generational screening. Those skilled in the art will recognize that the phenotypic identification of this in cis pairing is possible, but it will be apparent that the molecular identification method described herein is a faster and much more efficient method to identify this useful combination of alleles.

In January of 2000, five hundred four F2 seedlings, derived from the selfing of F1 hybrid 1652817, were sampled for DNA extraction (example 3), and the genotype at the Ty locus was determined for each sample using methods described herein (examples 4 and 5). One hundred twenty seven plants were homozygous for the susceptible '+' allele; these plants were discarded. The remaining three hundred seventy seven plants that were either heterozygous for the Ty-1 allele (Ty-1/'+') or homozygous for the Ty-1 allele (Ty-1/Ty-1) were analyzed by methods described herein (examples 4, 6, 7) to determine the genotype at the nearby Mi locus. Any plant containing one favorable allele as a heterozygote (either Ty-1 or Mi-1) and having the other favorable allele (either Ty-1 or Mi-1) fixed as a homozygote were selected as having the Ty-1 and Mi-1 alleles in cis.

Recombinants were not expected, as it has been well documented that recombination is suppressed in this region of chromosome 6. Thus, it was unexpected that eight such recombinants were discovered. Kaloshian et al. ((1998) Mol. Gen. Genet. 257:376-385), showed that the recombination frequency in this region was approximately 8-fold higher when peruvianum by peruvianum crosses were made compared with *esculentum* by peruvianum crosses. Even with this possible explanation for a relatively high recovery of recombinants, it was still unexpected because the cross made contains hirsutum and peruvianum DNA in this genome region, and not the peruvianum by peruvianum crosses of Kaloshian et al. (ibidem).

The Mi-1 and Ty-1 introgressions are known to cause genetic drag separately. Therefore, because each of the 8 recombinants discovered likely are unique recombinational events, this was an opportunity to reduce drag associated with introgressing these traits. Considerable horticultural evaluations were made and from these evaluations, two plants, designated #20 and #251 were selected for advancement. Both of these plants were heterozygous for the Ty-1 allele (Ty-1/'+') and homozygous for the Mi-1 allele. Both these plants, therefore, contain the Ty-1 and Mi alleles in cis, although this favorable in cis combination is not fixed.

In the spring of 2000, F2 plant numbers 20 and 251 were self-pollinated to create F3 populations. These populations were designated 97.5281.M20 and 97.5281.M251, respectively. Using methods described herein (examples 3-7), the Ty-1 and Mi-1 alleles were fixed in the homozygous condition for both events.

To ensure that the molecular testing accurately predicted the resistance phenotype, these fixed lines derived from plant #20 and #251 (97.5281.M20.M.1.1, 97.5281.M251.M.1.1, 97.5281.M251.M.2.1) were tested for root knot nematode resistance according to methodology described herein (example 1). Table 2 shows that these lines, having the unique in cis arrangement of the Ty-1 and Mi-1 alleles, were highly resistant to root knot nematodes.

These same lines (97.5281.M20.M.1.1, 97.5281.M251.M.1.1, 97.5281.M251.M.2.1) were also tested for TYLCV in Antalya, Turkey, using methodology described herein (example 2). These lines, having the unique in cis arrangement of the Ty-1 and Mi-1 alleles, were resistant to TYLCV.

This combination of the Ty-1 and Mi-1 efficacious resistance alleles in cis allows tomato breeders to create tomato hybrids that are resistant to TYLCV and highly resistant to nematodes, while retaining the freedom of having a second inbred parent to either mask the genetic drag, or delivering additional resistance genes for *Oidium*, or *Cladosporium*, or yet to be discovered resistance alleles in this disease cluster. This novel approach provides the tomato grower the opportunity to control a number of disease pathogens, with acceptable horticultural qualities without relying exclusively on chemical pesticides for control, or relying on transgenic resistance strategies.

What is claimed is:

1. A method of growing a seed from a first *Lycopersicon esculentum* plant comprising:
   a) providing said seed of said first *Lycopersicon esculentum* plant wherein said plant comprises within its genome at least one Ty-1 tomato yellow leaf curl virus (TYLCV) resistance allele and at least one Mi-1 root knot nematode resistance allele, wherein the at least one Ty-1 allele and the at least one Mi-1 allele are present in the coupling phase at different loci on one chromosome and said plant is resistant against TYLCV and resistant against at least one root knot nematode species selected from the group consisting of *Meloidogyne arenaria*, *Meloidogyne incognita* and *Meloidogyne javanica*; and
   b) growing said seed to provide a second *Lycopersicon esculentum* plant having a fruit.

2. The method of claim 1, wherein said first *Lycopersicon esculentum* plant has a root knot nematode resistance score of less than about 0.1.

3. The method of claim 1, wherein said first *Lycopersicon esculentum* plant has a root knot nematode resistance score of less than about 0.05.

4. The method of claim 1, wherein said first *Lycopersicon esculentum* plant has a root knot nematode resistance score of less than about 0.04.

5. The method of claim 1, wherein said first *Lycopersicon esculentum* plant has a root knot nematode resistance score of less than about 0.03.

6. The method of claim 1, wherein said one chromosome is chromosome 6.

7. The method according to claim 1, wherein said TYLCV resistance allele and said root knot nematode resistance allele are non-transgenic.

8. The method according to claim 1, wherein said TYLCV resistance allele and said root knot nematode resistance allele are from *Lycopersicon chilense* and from *Lycopersicon peruvianum*, respectively.

9. The method of claim 1, further comprising obtaining a second seed from said fruit, wherein said second seed comprises within its genome at least one Ty-1 yellow leaf curl virus (TYLCV) resistance allele and at least one Mi-1 root knot nematode resistance allele, wherein the at least one Ty-1 allele and the at least one Mi-1 allele are present in the coupling phase at different loci on one chromosome.

10. The method of claim 9, further comprising growing said second seed to provide a third *Lycopersicon esculentum* plant and crossing said third *Lycopersicon esculentum* plant with a fourth *Lycopersicon esculentum* plant.

11. A *Lycopersicon esculentum* plant obtained by the method of claim 10 comprising within its genome at least one tomato yellow leaf curl virus (TYLCV) resistance allele and at least one root knot nematode resistance allele, wherein said resistance alleles are present in the coupling phase at different loci on one chromosome and said plant is resistant against TYLCV and resistant against at least one root knot nematode species selected from the group consisting of *Meloidogyne arenaria*, *Meloidogyne incognita* and *Meloidogyne javanica*, and said at least one root knot nematode resistance allele is an allele designated as Mi-1.

12. The plant according to claim 11, wherein said plant has a root knot nematode resistance score of less than about 0.1.

13. The plant according to claim 11, wherein said TYLCV resistance allele is the allele designated as Ty-1.

14. A *Lycopersicon esculentum* seed obtained by the method of claim 9, comprising within its genome at least one tomato yellow leaf curl virus (TYLCV) resistance allele and at least one root knot nematode resistance allele, wherein said resistance alleles are present in the coupling phase at different loci on one chromosome and in that said plant is resistant against TYLCV and highly resistant to at least one root knot nematode species selected from *Meloidogyne arenaria*, *Meloidogyne incognita* and *Meloidogyne javanica*, wherein said root knot nematode resistance allele is an allele designated as Mi-1.

15. The seed according to claim 14, wherein said plant has a root knot nematode resistance score of less than about 0.1.

16. The seed according to claim 14, wherein said TYLCV resistance allele is the allele designated as Ty-1.

17. A method of making a disease resistant *L. esculentum* plant comprising the steps of:
   a. obtaining a first parent *L. esculentum* plant comprising within its genome an introgression at the Ty locus from *Lycopersicon chilense* on chromosome 6;
   b. crossing said first parent *L. esculentum* plant with a second parent *L. esculentum* plant that comprises an Mi-1 introgression from *Lycopersicon peruvianum* on said chromosome 6; and
   c. selecting a progeny *L. esculentum* plant comprising said introgressions from *L. chilense* and *L. peruvianum* coupled in cis on chromosome 6.

18. The method of claim 17, wherein said introgression at the Ty locus from *Lycopersicon chilense* on chromosome 6 and said Mi-1 introgression from *Lycopersicon peruvianum* on said chromosome 6 overcome suppressed recombination in the Mi/Ty region of chromosome 6.

19. A method of making a disease resistant *L. esculentum* plant comprising the steps of:
   a. obtaining a first parent *L. esculentum* plant comprising within its genome a Ty-1 introgression from *Lycopersicon chilense on chromosome* 6;
   b. crossing said first parent *L. esculentum* plant with a second parent *L. esculentum* plant that comprises a Mi-1 introgression from *Lycopersicon peruvianum* on said chromosome 6; and
   c. selecting a progeny *L. esculentum* plant comprising said Ty-1 introgression and said Mi-1 introgression coupled in cis.

20. The method of claim 1, wherein said first *Lycopersicon esculentum* plant is homozygous for said genome having at least one Ty-1 tomato yellow leaf curl virus (TYLCV) resistance allele and at least one Mi-1 root knot nematode resistance allele, wherein the at least one Ty-1 allele and the at least one Mi-1 allele are present in the coupling phase at different loci on one chromosome.

21. A method of producing a *Lycopersicon esculentum* fruit comprising:
   a) planting a *Lycopersicon esculentum* seed wherein said seed comprises within its genome at least one Ty-1 tomato yellow leaf curl virus (TYLCV) resistance allele and at least one Mi-1 root knot nematode resistance allele, wherein the at least one Ty-1 allele and the at least one Mi-1 allele are present in the coupling phase at different loci on one chromosome; and b) growing said seed to provide a *Lycopersicon esculentum* plant having a fruit, wherein said *Lycopersicon esculentum* plant is resistant against TYLCV and resistant against at least one root knot nematode species selected from the group consisting of *Meloidogyne arenaria, Meloidogyne incognita* and *Meloidogyne javanica.*

22. The method of claim 21, wherein said one chromosome is chromosome 6.

23. The method according to claim 21, wherein said TYLCV resistance allele and said root knot nematode resistance allele are non-transgenic.

24. The method according to claim 21, wherein said TYLCV resistance allele and said root knot nematode resistance allele are from *Lycopersicon chilense* and from *Lycopersicon peruvianum*, respectively.

25. The method according to claim 21, further comprising harvesting said fruit.

26. A *Lycopersicon esculentum* fruit obtained by the method of claim 21, comprising within its genome at least one tomato yellow leaf curl virus (TYLCV) resistance allele and at least one root knot nematode resistance allele, wherein said resistance alleles are present in the coupling phase at different loci on one chromosome.

27. The *Lycopersicon esculentum* fruit according to claim 26, wherein said TYLCV resistance allele is the allele designated as Ty-1.

28. The *Lycopersicon esculentum* fruit according to claim 26, wherein said root knot nematode resistance allele is the allele designated as Mi-1.

* * * * *

SEQUENCE LISTING

```
<160> NUMBER OF SEQ ID NOS: 11

<210> SEQ ID NO 1
<211> LENGTH: 22
<212> TYPE: DNA
<213> ORGANISM: Lycopersicon esculentum

<400> SEQUENCE: 1
taatccgccg ttacctctcc tt                                              22
```

<210> SEQ ID NO 2
<211> LENGTH: 22
<212> TYPE: DNA
<213> ORGANISM: Lycopersicon esculentum

<400> SEQUENCE: 2
cggatgactt caatagcaat ga                                              22

<210> SEQ ID NO 3
<211> LENGTH: 22
<212> TYPE: DNA
<213> ORGANISM: Lycopersicon peruvianum

<400> SEQUENCE: 3
aaccgtggac tttgctttga ct                                              22

<210> SEQ ID NO 4
<211> LENGTH: 24
<212> TYPE: DNA
<213> ORGANISM: Lycopersicon esculentum

<400> SEQUENCE: 4
taagaacagg gactcagagg atga                                            24

<210> SEQ ID NO 5
<211> LENGTH: 21
<212> TYPE: DNA
<213> ORGANISM: Lycopersicon esculentum

<400> SEQUENCE: 5
ctacggagga tgcaaataga a                                               21

<210> SEQ ID NO 6
<211> LENGTH: 23
<212> TYPE: DNA
<213> ORGANISM: Lycopersicon esculentum

<400> SEQUENCE: 6
aatcattatt gtcacacttc ccc                                             23

<210> SEQ ID NO 7
<211> LENGTH: 916
<212> TYPE: DNA
<213> ORGANISM: Lycopersicon esculentum

<400> SEQUENCE: 7
gacacggacc cactattctg aaactgatgg tcattctttc tctccttatc ggagccttgg     60
tctgagtttc cagtcttgca agcaaagtga ctagcttgac gtaagggatc tgcacttaca    120
tcggtatcct gttgagttgc ataaccagaa accatggact ttgctttgac ttttttacct    180
gattcacgat gaacatcttt ctcctctaat tcagcttcag ataatagatc ataactcttg    240
ccattgcagg cattatcctt cttaaccata ctggatttat tggagaacac atcatttca     300 ccatcagaag acctcttggg actagaagtg gtaaggctg aagagggagc aacagaaggt     360
cgcgaattgc atagatcctt ttgtgaagaa tctgcagctt taacactcaa caaagataga    420
gtactatcca gatcttgccc agcctgctgt tccttttaa cttgacctgt tccagcacta     480
cctttgcttg cactagtgtc cttccggtca gacaaggaga cccttgctac cttttccttc    540
ctagagatgt catcacatat tttttccata gaatcctggg gattacatgt caaggaatct    600
cgcagttctc tccctttct cttaatcgga gaatcattat tgtcacactt ccccttatgc    660

```
gttgacacat cggaaatata agcttctggg ttctttgctg aaaccaagtc tttcttgaa    720 tcatcctctg agtccctgtt cttacatttg tcacgaatca tctctggcat tttactgctt    780
gaactccatc tagactttc aacaacaggg caaaaggtct ggttctcgtc atcgagtgca    840
tcatcttgta aattttttt ggaagataca tctgattcca cttcacttgt gttccttcta    900
tttgcatcct ccgtag                                                   916
```

<210> SEQ ID NO 8
<211> LENGTH: 915
<212> TYPE: DNA
<213> ORGANISM: Lycopersicon peruvianum

<400> SEQUENCE: 8

```
gacacggacc cactattctg aaaccgatgg tcattctttc tctccttatc ggagccttgg     60
tctgaatttc ccgtcttgca agcaaattga ctagcttgac gtaagggatc tgcacttgca    120
tcggtatcct gttgagttgc ataaccagaa accgtggact ttgctttgac ttttttacct    180
gattcacgat ggacatcttt ctcctctaat tcagcttcag ataatagatc ataactcttg    240
ccattgcagg cattatcctt cttaaccata ctggatttat tggagaaccc atcattttca    300
ccatcagaag acctcttggc actagaagtg ggaaaggctg aagagggagc aacagaaggt    360
cgcgaattgc atagatcctt ttgtgaagaa tctgcagctt taacactcaa caaagataga    420
gtactatcca gatcttgccc agcctgctgt tcctttttaa cttgacctgt tccagcacta    480
cctttgcttg cactagtgtc cttccggtca gacaaggaga cccttgctac cttttccttc    540
ctggagatgt catcacatat ttttccata gaatcttggg gattacatgt caaggaatct    600
cgaagttctc tccctttct cttaatcgga gaatcattat tgtcacactt ccccttatgc    660
gttgacacat cggaaatata agcttctggg ttctttgctg aaaccaagtc tttcttgaa    720 tcatcctctg agtccctgtt cttacatttg tcacgaatca tctctggcat tttactgctt    780
gaactccatc tagactttc aacaacaggg cagaaggtct ggttctcgtc atcgagtgca    840
tcatctcgta aattttttt ggaagataca tctgattcca cctcacttgt gttccttcta    900
tttgcatcct ccgta                                                   915
```

<210> SEQ ID NO 9
<211> LENGTH: 916
<212> TYPE: DNA
<213> ORGANISM: Lycopersicon chilense

<400> SEQUENCE: 9

```
gacacggacc cactattctg aaactgatgg tcattctttc tctccttatc ggagccttgg     60
tctgactttc cagtcttgca agcaaattga ctagcttgac gtaagggatc tgcacttaca    120
tcggtatcct gttgagttgc ataaccagaa accgtggact ttgctttgac ttttttacct    180
gattcacgat ggacaacttt ctcctctaat tcagcttcag ataatagatc ataactcttg    240
ccattgcagg cattatcctt cttaaccata ctggatttat tggagaaccc atcattttca    300
ccatcagaag acctcttggg actagaagtg ggtaaggctg aagagggagc aacagaaggt    360
cgcgaattgc atagatcctt ttgtgaagaa tctgcagctt taacactcaa caaagataga    420
gtactatcca gatcttgccc agcctgctgt tcctttttaa cttgacctgt tccagcacta    480
cctttgcttg cactagtgtc cttccggtca gacaaggaga cccttgctac cttttccttc    540
```

```
ctggagatgt catcacatat tttttccata gaatcctggg gattacatgt caaggaatct      600
cgaagttctc tcccttttct cttaatcgga gaatcattat tgtcacactt cccttatgc      660 gttgacacat cggaaatata agcttctggg ttctttgctg aaaccaagtc tttctttgaa      720
tcatcctctg agtccctgtt cttacatttg tcatgaatca tctctggcat cttactgctt      780
gaactccatc tagacttttc aacaacaggg cagaaggtct ggttctcgtc atcgagtgca      840
tcatcttgta taatttttt ggaagataca tctgattcca cctcacttgt gttccttcta      900
tttgcatcct ccgtag                                                      916
```

<210> SEQ ID NO 10
<211> LENGTH: 406
<212> TYPE: DNA
<213> ORGANISM: Lycopersicon chilense
<220> FEATURE:
<221> NAME/KEY: N
<222> LOCATION: (328)..(328)
<223> OTHER INFORMATION: N is A, C, G, or T
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: N
<222> LOCATION: (368)..(368)
<223> OTHER INFORMATION: N is A, C, G, or T
<220> FEATURE:
<221> NAME/KEY: misc_feature
<222> LOCATION: (368)..(368)
<223> OTHER INFORMATION: n is a, c, g, or t

<400> SEQUENCE: 10

```
ctaatccgtc gttacctctc ctttgaacta aaatttttt gtcaaaagtt acaaatctgt       60
ttattttata tattttttt cttggaatta ctatcgatat ttttgtaatt agaaggttag      120
aattggagta tatatgttgt gattggaacg atttgttgtt gcctttatgg tggcaattat      180
gtttacatgt gtcattggct aacttactga gtcatcttac tttttaata agaatgcttc       240 aaatgtttat aatttcatta gctcaatggt aattgtattt attgatgcat atatcttttt      300
tgttctagtt tctgattata tcatgtancg aaacttatat aaaaaataat tagtaatagt      360
agtagaanat ttatgacatc attgctattg aagtcatccg gaatct                    406
```

<210> SEQ ID NO 11
<211> LENGTH: 407
<212> TYPE: DNA
<213> ORGANISM: Lycopersicon esculentum
<220> FEATURE:
<221> NAME/KEY: N
<222> LOCATION: (406)..(406)
<223> OTHER INFORMATION: N is A, C, G, or T
<220> FEATURE:
<221> NAME/KEY: misc_feature
<222> LOCATION: (406)..(406)
<223> OTHER INFORMATION: n is a, c, g, or t

<400> SEQUENCE: 11

```
ctaatccgtc gttacctctc ctttgaacta aaaatttgtt gtcaaaagtt acaaatctgt      60
ttattttata tacttttttc ttggaattac tatctttatt tttgtaatta gaaggttaga     120
attggagtat atatgttgtg attggaccga gttgctattg cctttatggt ggaaattatg     180
tttacatgtg tcatgggta acttactgag tcatcttact tttaataa gaatgcttca        240 tatgtttata attccattag ctcaatggtt attgtattta ttgatgcata tatcttttt     300
```

```
gttctagttt ctgattatat catgtagcga aacttatata aaaaataaat agtaatagta    360
gtagataatt atgacatcat tgctattgaa gtcatccgga atctanc                  407
```